United States Patent
Koka et al.

(10) Patent No.: US 11,452,866 B2
(45) Date of Patent: Sep. 27, 2022

(54) ELECTRODE LOCATING SYSTEMS AND METHODS FOR USE WITHIN A COCHLEAR IMPLANT PATIENT

(71) Applicant: Advanced Bionics AG, Staefa (CH)

(72) Inventors: Kanthaiah Koka, Valencia, CA (US); Leonid M. Litvak, Los Angeles, CA (US)

(73) Assignee: Advanced Bionics AG, Staefa (CH)

( * ) Notice: Subject to any disclaimer, the term of this patent is extended or adjusted under 35 U.S.C. 154(b) by 77 days.

(21) Appl. No.: 16/640,485

(22) PCT Filed: Aug. 31, 2017

(86) PCT No.: PCT/US2017/049792
§ 371 (c)(1),
(2) Date: Feb. 20, 2020

(87) PCT Pub. No.: WO2019/045747
PCT Pub. Date: Mar. 7, 2019

(65) Prior Publication Data
US 2020/0171301 A1    Jun. 4, 2020

(51) Int. Cl.
*A61N 1/05* (2006.01)
*A61N 1/36* (2006.01)
*A61N 1/08* (2006.01)

(52) U.S. Cl.
CPC ............. *A61N 1/0541* (2013.01); *A61N 1/08* (2013.01); *A61N 1/36038* (2017.08); *A61N 1/36039* (2017.08); *A61N 2001/083* (2013.01)

(58) Field of Classification Search
CPC .... A61N 1/0541; A61N 1/08; A61N 1/36038; A61N 2001/083; A61B 5/063
(Continued)

(56) References Cited

U.S. PATENT DOCUMENTS

| 8,532,781 B1 | 9/2013 | Vanpoucke |
| 9,597,495 B2 | 3/2017 | Greenberg et al. |

(Continued)

FOREIGN PATENT DOCUMENTS

| WO | 2015168388 | 11/2015 |
| WO | 2017182931 | 10/2017 |

OTHER PUBLICATIONS

International Search Report and Written Opinion received in International Application No. PCT/US17/049792, dated Apr. 26, 2018.
(Continued)

*Primary Examiner* — Carl H Layno
*Assistant Examiner* — Jane C Kalinock
(74) *Attorney, Agent, or Firm* — ALG Intellectual Property, LLC

(57) ABSTRACT

An exemplary electrode locating system performs an excitation spread measurement by directing a first electrode to generate an electrical pulse and, in response to the generation of the electrical pulse, detecting a voltage between a second electrode and a reference that are both distinct from the first electrode. The first and second electrodes are included in a plurality of electrodes disposed on an electrode lead included within a cochlear implant system and that comprises a proximal portion configured to be coupled with a cochlear implant and a distal portion configured to be inserted into a cochlea of a patient by way of an insertion procedure. Based on the excitation spread measurement, the electrode locating system determines whether at least one of the first electrode and the second electrode is located within the cochlea. Corresponding methods are also described.

20 Claims, 11 Drawing Sheets

(58) Field of Classification Search
USPC .......................................................... 607/137
See application file for complete search history.

(56) References Cited

U.S. PATENT DOCUMENTS

| | | | |
|---|---|---|---|
| 9,597,503 B2 | 3/2017 | Risi et al. | |
| 2005/0203590 A1* | 9/2005 | Zierhofer | H04R 25/505 |
| | | | 607/57 |
| 2011/0077712 A1* | 3/2011 | Killian | A61B 5/12 |
| | | | 607/57 |
| 2012/0316454 A1 | 12/2012 | Carter | |
| 2015/0314122 A1* | 11/2015 | Kabot | A61N 1/08 |
| | | | 607/137 |
| 2016/0059014 A1 | 3/2016 | Johnston et al. | |
| 2018/0369571 A1* | 12/2018 | Landsberger | A61N 1/36039 |

OTHER PUBLICATIONS

Holden, et al., Factors Affecting Open-Set Word Recognition in Adults with Cochlear Implants, Ear Hear. 2013; 34 (3): 342-360.

Noble, et al., Image-guidance enables new methods for customizing cochlear implant stimulation strategies, IEEE Trans Neural Syst Rehabil Eng. Sep. 2013; 21(5): 820-829.

* cited by examiner

ELECTRODE LOCATING SYSTEMS AND METHODS FOR USE WITHIN A COCHLEAR IMPLANT PATIENT

BACKGROUND INFORMATION

Cochlear implant systems are used to provide, restore, and/or improve hearing loss suffered by cochlear implant patients who use the cochlear implant systems. A key component of a cochlear implant system is an electrode lead that is inserted into a cochlea of the patient in a delicate surgical procedure referred to herein as an "insertion procedure." Because insertion procedures are difficult and may result in cochlear trauma or other harm if not done with extreme care, surgeons and other people involved in insertion procedures may desire to carefully monitor and track the electrode lead and its position (i.e., its insertion depth) with respect to the cochlea both during the insertion procedure as well as after the insertion procedure is complete. For example, by knowing which electrodes (e.g., on an electrode lead that includes a plurality of electrodes) have entered the cochlea and which electrodes are still external to the cochlea, the surgeon or surgical team may more easily and conveniently perform a safe, effective surgical insertion of the electrode lead, thereby resulting in desirable hearing outcomes for patients.

Unfortunately, current methods for locating electrodes of an electrode lead within patients typically involve imaging technology (e.g., x-ray technology, fluoroscopic technology, CT scanning technology, etc.) that is expensive, inconvenient, and may expose patients to undesirable risk. Moreover, these current methods for locating electrodes may be impractical or impossible to employ during insertion procedures, when electrode locating may be of most value for ensuring proper procedures and securing positive outcomes. For instance, even if the surgeon performing an insertion procedure is generally aware of the approximate position of the electrode lead at any given point during an insertion procedure, other people involved in the procedure (e.g., doctors, nurses, fellows, etc., who are assisting with the procedure) may be unaware of electrode locations, inhibiting their ability to effectively assist the surgeon in performing the insertion procedure effectively and safely.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
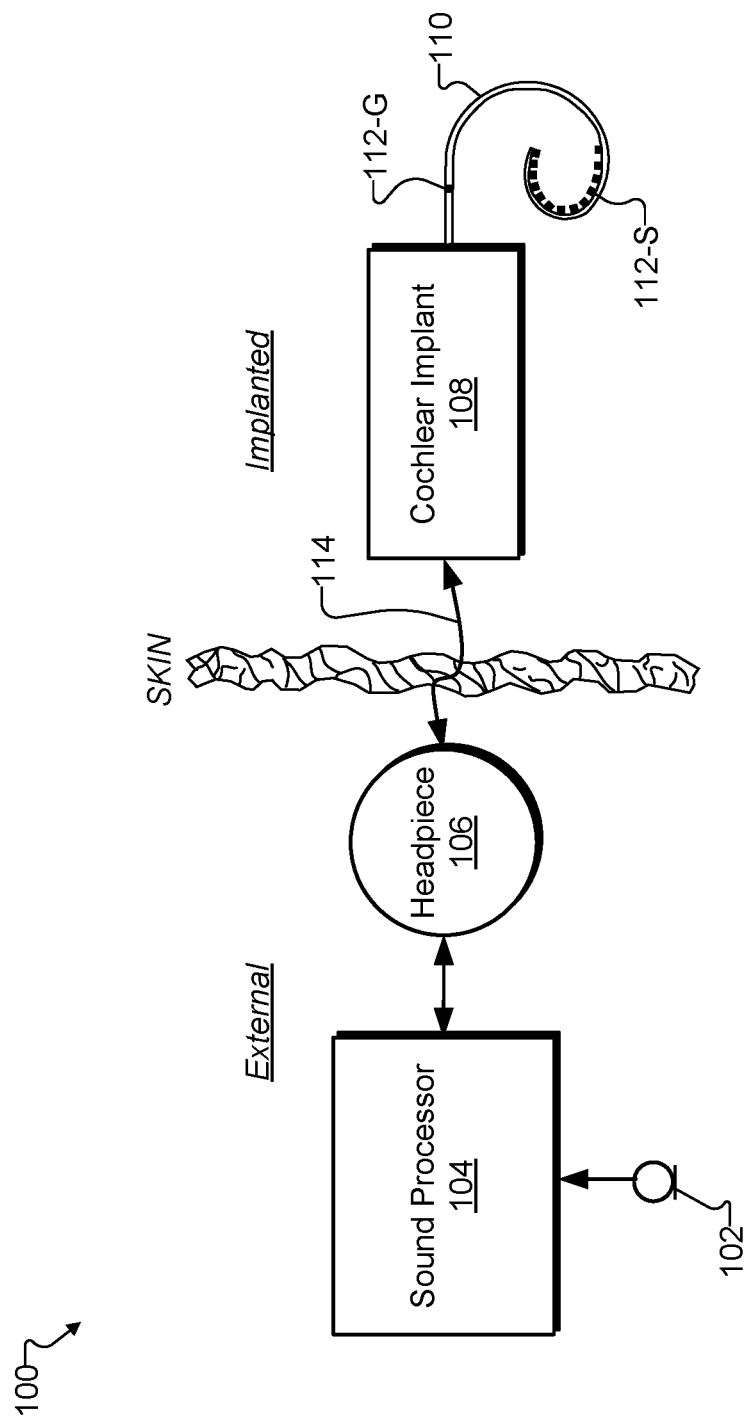
FIG. 1 illustrates an exemplary cochlear implant system according to principles described herein.

Electrode locating systems and methods for use within a cochlear implant patient are described herein. In other words, systems and methods for determining or detecting a relative location (e.g., relative to the cochlea of a cochlear implant patient) of particular electrodes included on an electrode lead, and/or a relative insertion depth of the electrode lead itself, will be described. For example, as described below, disclosed systems and methods may locate electrodes as being located within or external to a cochlea of a patient (e.g., in real time during an insertion procedure in which an electrode lead including the electrodes is being inserted into the cochlea).

To this end, in one implementation, an exemplary electrode locating system implemented by at least one physical computing device (e.g., by a computing system coupled to a cochlear implant system, by a sound processor included within a cochlear implant system, by a combination of a computing system and a sound processor included within a cochlear implant system, etc.) may perform an excitation spread measurement. As used herein, an "excitation spread measurement" may refer to any measurement configured to determine the extent to which stimulation (e.g., a electrical pulse) applied by one electrode at one location may spread or travel (e.g., through fluid and/or tissue at and surrounding the location) so as to be detectable (e.g., as a voltage) by another electrode at another location. As such, an excitation spread measurement as performed by the systems and methods described herein may be similar to a conventional impedance measurement in which stimulation is applied by an electrode and then detected by the same electrode (e.g., with reference to a ground electrode, with reference to another separate stimulating electrode, etc.). However, in contrast with conventional impedance measurements, excitation spread measurements as performed by the systems and methods described herein may apply stimulation with a different and distinct electrode from the electrode used to detect or record the stimulation (e.g., a voltage resulting from the application of the stimulation) as the stimulation spreads. As such, in some examples, an excitation spread measurement may also be referred to as a "cross impedance" measurement or the like.

As one example of how an excitation spread measurement may be performed, the electrode locating system may direct a first electrode to generate an electrical pulse and, in response to the generation of the electrical pulse, may detect a voltage between a second electrode (e.g., an electrode that may also be used as a stimulating electrode or a ground electrode) and a reference (e.g., a ground electrode, a case ground of a cochlear implant device, etc.) where both the second electrode and the reference are distinct from the first electrode. The first and second electrodes may each be included in a plurality of electrodes disposed on an electrode lead included within a cochlear implant system. In particular, the electrode lead may include a proximal portion configured to be coupled with a cochlear implant, as well as a distal portion configured to be inserted into a cochlea of a patient by way of an insertion procedure. Based on the excitation spread measurement, the electrode locating system may determine whether at least one of the first electrode and the second electrode is located within the cochlea.

In certain implementations, the electrode locating system may perform one or more of the operations described above on each electrode in the plurality of electrodes, or at least on each electrode included on the distal portion of the electrode lead that is to be inserted into the cochlea of the patient. In this way, the electrode locating system may detect enough information to determine not only a location for each electrode, but also to determine an insertion depth of the electrode lead as a whole. For example, at a point in time during an insertion procedure, the electrode locating system may determine that the electrode lead is located in a position in which the first X number of electrodes have been inserted into the cochlea while the remaining Y number of electrodes are still external to the cochlea (where the sum of X and Y is the total number of electrodes disposed on the electrode lead).

Specifically, for instance, an electrode locating system may perform (e.g., in real time during the insertion procedure) a sequence of excitation spread measurements involving electrodes disposed on the distal portion of the electrode lead. Each excitation spread measurement in the sequence of excitation spread measurements may be performed by directing a first electrode to generate an electrical pulse (i.e., where the first electrode is included in a plurality of electrodes disposed on the electrode lead that includes the electrodes disposed on the distal portion of the electrode lead as well as, potentially, other electrodes such as a ground electrode disposed on a proximal portion of the electrode lead), and, in response to the generation of the electrical pulse, detecting a voltage between a second electrode included within the plurality of electrodes and a reference, where both the second electrode and the reference are distinct from the first electrode. Based on the sequence of excitation spread measurements, the electrode locating system may determine (e.g., still in real time during the insertion procedure) whether each of the electrodes disposed on the distal portion of the electrode lead is located within the cochlea. Subsequently, based on the determination of whether each of the electrodes disposed on the distal portion of the electrode lead is located within the cochlea, the electrode locating system may determine, in real time during the insertion procedure, an insertion depth of the electrode lead within the cochlea (e.g., a location of the electrode lead relative to the cochlea).

Electrode locating systems and methods described herein may provide various benefits to cochlear implant patients, as well as to surgeons and others involved with insertion procedures. For example, by providing information about whether particular electrodes are located within the cochlea during an insertion procedure (e.g., in real time), disclosed electrode locating systems and methods may provide a surgeon performing the insertion procedure more visibility and perspective into the intricate procedure, thereby facilitating a successful outcome with the insertion procedure.

Even if a surgeon may have some awareness of where various electrodes disposed on an electrode lead are located during an insertion procedure without employing electrode locating systems and methods described herein (e.g., based on the surgeon's experience, etc.), disclosed electrode locating systems and methods may provide more accurate, fine-tuned, and/or updated information than the surgeon may be able to discern from experience alone. Moreover, disclosed electrode locating systems and methods may provide those assisting the surgeon (e.g., nurses, other doctors, etc.) with visibility into the electrode location. In this manner, those assisting the surgeon may not have to rely on verbal updates explicitly provided by the surgeon during the insertion procedure (e.g., which may be inconvenient for the surgeon to consistently provide and/or which the surgeon may neglect to consistently provide). Thus, by providing assistants with a real-time view into the progress of the insertion procedure, the surgeon may be freed up from having to provide verbal updates as to the procedure status, while the assistants may be enabled to more effectively assist the surgeon in the procedure by, for example, anticipating upcoming challenges, talking the surgeon through especially difficult parts of the insertion procedure (e.g., instructing the surgeon to proceed with caution in places where previous insertion procedures have resulted in cochlear trauma in other patients, etc.), and so forth.

Along with providing visibility into the insertion procedure for personnel assisting with the insertion procedure, disclosed electrode locating systems and methods may further provide data representative of electrode locations and electrode lead insertion depths to computer systems used to facilitate the insertion procedure. This may allow the computer systems to provide feedback or warnings (e.g., by way of user interfaces, lights, sounds, etc.) that may help the surgeon and other people involved in performing the insertion procedure to proceed with appropriate care at various stages of the procedure. Moreover, in situations where significant events such as cochlear trauma are detected to have occurred during a particular insertion procedure, computer systems with an awareness of electrode location may log information representative of the progress of the procedure when the events occurred. Such information may be useful in subsequent procedures for other cochlear implant patients (e.g., to warn surgeons to take particular care or to perform particular actions when an electrode lead is located at a location that has previously been problematic).

Even after an insertion procedure is complete, disclosed electrode locating systems and methods may be useful for providing insight into a final resting location at which the electrode lead has been inserted. For example, the electrode locating systems and methods described herein may help ensure, subsequent to an insertion procedure, that all of the stimulating electrodes on an electrode lead have been successfully inserted into a cochlea of a patient, and that each electrode has a good connection within the cochlea (e.g., by way of fluid conduction paths in the cochlea).

Moreover, by performing excitation spread measurements between a first electrode that applies the electrical pulse and a second, different electrode that detects the spread of the electrical pulse (i.e., with respect to the reference), more accurate measurements may be obtained than by, for example, performing conventional impedance measurements where the same electrode is configured to take part in both applying an electrical pulse and detecting a voltage resulting from the electrical pulse. This is at least in part because the same electrode may be incapable of applying and detecting stimulation at the same time. As such, in a conventional impedance measurement, an electrode may be used to generate an electrical pulse and then, after a certain amount of time (e.g., an amount of time that it takes to switch the electrode from operating in a stimulation mode to operating in a detection mode), to detect a voltage resulting from the electrical pulse as the pulse spreads through the tissue and/or fluid surrounding the electrode in accordance with the impedance of the tissue and/or fluid. In contrast, because excitation measurements as performed by the systems and methods described herein may involve two separate electrodes along with a separate reference distinct from either electrode, one electrode may generate electrical stimulation (e.g., one or more electrical pulses) while the other electrode detects the excitation spread of the stimulation (e.g., by detecting a voltage) with respect to the reference simultaneously. This simultaneity may reduce an undesirable delay between stimulation being applied and a resulting voltage being detected to thereby make such excitation spread measurements more accurate and/or reliable than similar impedance measurements.

Another advantage of not using the same electrode to apply stimulation and detect a voltage resulting from the stimulation, as opposed to conventional impedance measurements that use the same electrode to both apply and detect, is that the risk of obtaining a false positive measurement may be reduced. As used herein, a "false positive" may refer to a measurement (e.g., an excitation spread measurement) that indicates that a particular electrode is located within the cochlea even though it is not. This is because the closer an electrode is to the cochlea, the more likely it is that the electrode will be in contact with at least some fluid associated with the cochlea. If, for example, a particular electrode is in contact with fluid associated with the cochlea, but not actually within the cochlea, a false positive may be detected if the particular electrode is used to apply an electrical pulse and then detect a voltage that occurs as a result of the electrical pulse. In contrast, if the detecting electrode and the reference are relatively far from the cochlea, the likelihood of a false positive may be reduced because the detecting electrode and reference are likely not also in contact with the fluid.

Various embodiments will now be described in more detail with reference to the figures. The disclosed systems and methods may provide one or more of the benefits mentioned above and/or various additional and/or alternative benefits that will be made apparent herein.

FIG. 1 illustrates an exemplary cochlear implant system 100. As shown, cochlear implant system 100 may include a microphone 102, a sound processor 104, a headpiece 106 having a coil disposed therein, a cochlear implant 108, and an electrode lead 110. Electrode lead 110 may include a plurality of electrodes 112. In particular, electrodes 112 may include an array of stimulating electrodes 112-S (also referred to as intracochlear electrodes) disposed on a distal portion of electrode lead 110 and that are configured to be located within and to stimulate the cochlea after the distal portion of electrode lead 110 is inserted into the cochlea. As shown, electrode lead 110 may also include a ground electrode 112-G (also referred to as a ring electrode) disposed on a proximal portion of electrode lead 110 and that is configured provide a current return path for stimulation current generated by electrodes 112-S and to remain external to the cochlea after electrode lead 110 is inserted into the cochlea. While a single ground electrode 112-G is shown in FIG. 1, it will be recognized that multiple ground electrodes 112-G may be disposed on the proximal portion of electrode lead 110 as may serve a particular implementation. As shown, electrode lead 110 may be pre-curved so as to properly fit within the spiral shape of the cochlea. Additional or alternative components may be included within cochlear implant system 100 as may serve a particular implementation.

As shown, cochlear implant system 100 may include various components configured to be located external to a patient including, but not limited to, microphone 102, sound processor 104, and headpiece 106. Cochlear implant system 100 may further include various components configured to be implanted within the patient including, but not limited to, cochlear implant 108 and electrode lead 110.

Microphone 102 may be configured to detect audio signals presented to the user. Microphone 102 may be implemented in any suitable manner. For example, microphone 102 may include a microphone that is configured to be placed within the concha of the ear near the entrance to the ear canal, such as a T-MIC™ microphone from Advanced Bionics. Such a microphone may be held within the concha of the ear near the entrance of the ear canal by a boom or stalk that is attached to an ear hook configured to be selectively attached to sound processor 104. Additionally or alternatively, microphone 102 may be implemented by one or more microphones disposed within headpiece 106, one or more microphones disposed within sound processor 104, one or more beam-forming microphones, and/or any other suitable microphone as may serve a particular implementation.

Sound processor 104 (i.e., one or more components included within sound processor 104) may be configured to direct cochlear implant 108 to generate and apply electrical stimulation (also referred to herein as "stimulation current") representative of one or more audio signals (e.g., one or more audio signals detected by microphone 102, input by way of an auxiliary audio input port, input by way of a clinician's programming interface ("CPI") device, etc.) to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. To this end, sound processor 104 may process the one or more audio signals in accordance with a selected sound processing strategy or program to generate appropriate stimulation parameters for controlling cochlear implant 108. Sound processor 104 may be housed within any suitable housing (e.g., a behind-the-ear ("BTE") unit, a body worn device, headpiece 106, and/or any other sound processing unit as may serve a particular implementation).

In some examples, sound processor 104 may wirelessly transmit stimulation parameters (e.g., in the form of data words included in a forward telemetry sequence) and/or power signals to cochlear implant 108 by way of a wireless communication link 114 between headpiece 106 and cochlear implant 108 (e.g., a wireless link between a coil disposed within headpiece 106 and a coil physically coupled to cochlear implant 108). It will be understood that communication link 114 may include a bi-directional communication link and/or one or more dedicated uni-directional communication links.

Headpiece 106 may be communicatively coupled to sound processor 104 and may include an external antenna (e.g., a coil and/or one or more wireless communication components) configured to facilitate selective wireless coupling of sound processor 104 to cochlear implant 108. Headpiece 106 may additionally or alternatively be used to selectively and wirelessly couple any other external device to cochlear implant 108. To this end, headpiece 106 may be configured to be affixed to the patient's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or power signals may be wirelessly transmitted between sound processor 104 and cochlear implant 108 via a communication link 114 (which may include a bi-directional communication link and/or one or more dedicated uni-directional communication links as may serve a particular implementation).

Cochlear implant 108 may include any type of implantable stimulator that may be used in association with the systems and methods described herein. For example, cochlear implant 108 may be implemented by an implantable cochlear stimulator. In some alternative implementations, cochlear implant 108 may include a brainstem implant and/or any other type of cochlear implant that may be implanted within a patient and configured to apply stimulation to one or more stimulation sites located along an auditory pathway of a patient.

In some examples, cochlear implant 108 may be configured to generate electrical stimulation representative of an audio signal processed by sound processor 104 (e.g., an audio signal detected by microphone 102) in accordance with one or more stimulation parameters transmitted thereto by sound processor 104. Cochlear implant 108 may be further configured to apply the electrical stimulation to one or more stimulation sites (e.g., one or more intracochlear regions) within the patient via electrodes 112 disposed along electrode lead 110 (e.g., applying current by way of stimulating electrodes 112-S that returns by way of ground electrode 112-G). In some examples, cochlear implant 108 may include a plurality of independent current sources each associated with a channel defined by one or more of electrodes 112. In this manner, different stimulation current levels may be applied to multiple stimulation sites simultaneously by way of multiple electrodes 112.

Figure 2:
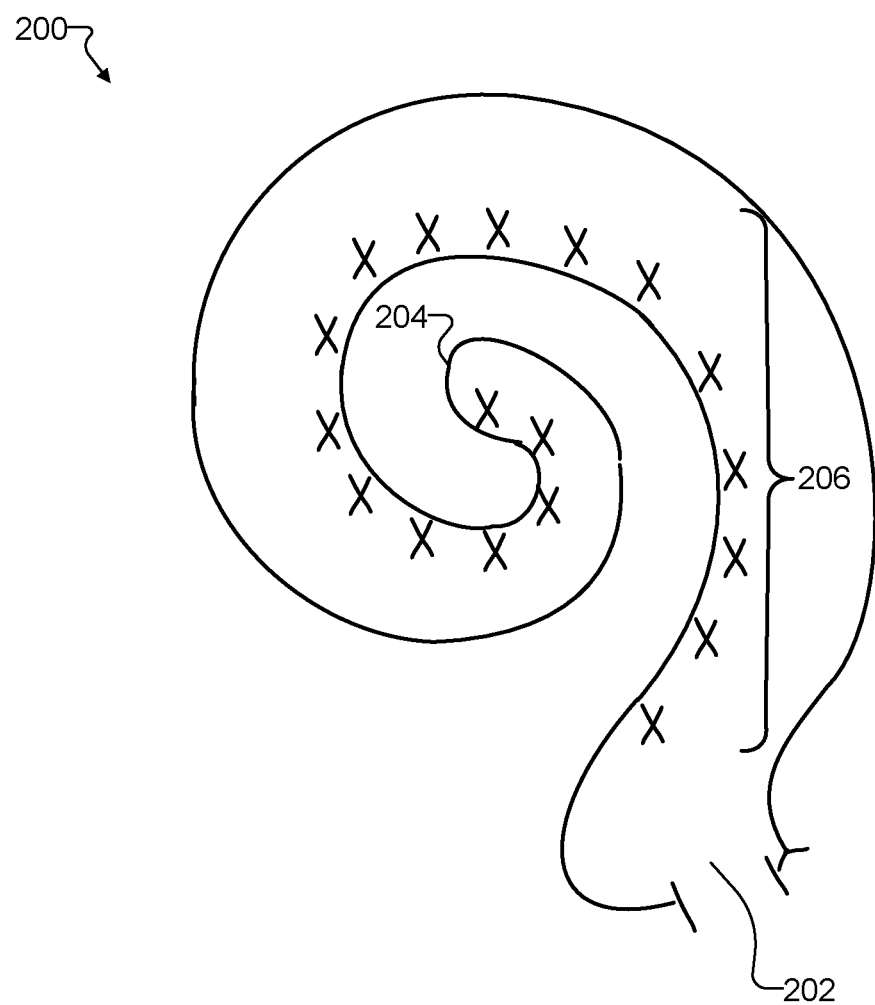
FIG. 2 illustrates a schematic structure of the human cochlea according to principles described herein.

FIG. 2 illustrates a schematic structure of the human cochlea 200 into which electrode lead 110 may be inserted. As shown in FIG. 2, cochlea 200 is in the shape of a spiral beginning at a base 202 and ending at an apex 204. Within cochlea 200 resides auditory nerve tissue 206, which is denoted by Xs in FIG. 2. The auditory nerve tissue 206 is organized within the cochlea 200 in a tonotopic manner. Relatively low frequencies are encoded at or near the apex 204 of the cochlea 200 (referred to as an "apical region") while relatively high frequencies are encoded at or near the base 202 (referred to as a "basal region"). Hence, electrical stimulation applied by way of electrodes disposed within the apical region (i.e., "apical electrodes") may result in the patient perceiving relatively low frequencies and electrical stimulation applied by way of electrodes disposed within the basal region (i.e., "basal electrodes") may result in the patient perceiving relatively high frequencies. The delineation between the apical and basal electrodes on a particular electrode lead may vary depending on the insertion depth of the electrode lead, the anatomy of the patient's cochlea, and/or any other factor as may serve a particular implementation.

In some examples, at least one computing device (e.g., a programming system, etc.) that is separate from (i.e., not included within) cochlear implant system 100 may be communicatively coupled to sound processor 104 in order to facilitate proper insertion of electrode lead 110 into a cochlea of a patient during a surgical insertion procedure, to perform one or more programming or fitting operations with respect to cochlear implant system 100, or for other suitable purposes as may serve a particular implementation. For example, during the insertion procedure, the at least one physical computing device may direct cochlear implant system 100 to perform operations (e.g., excitation spread measurements, electrode location determinations based on the excitation spread measurements, etc.) for locating electrodes 112 on electrode lead 110 within the patient. Subsequent to the insertion procedure, the at least one physical computing device may be used to present audio clips to the patient by way of cochlear implant system 100 in order to facilitate evaluation of how well cochlear implant system 100 is performing for the patient. In other examples, any of these operations may be performed by components of cochlear implant system 100 (e.g., by sound processor 104) without interaction with an external computing device.

Figure 3:
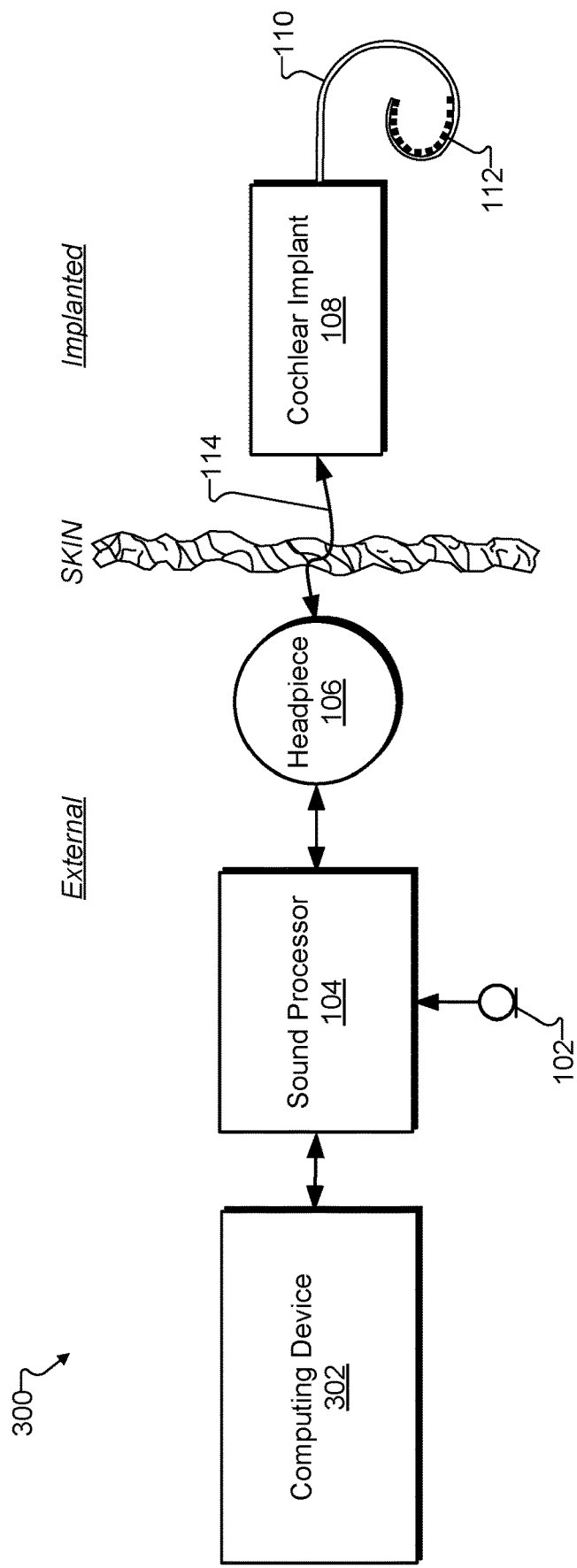
FIG. 3 illustrates an exemplary configuration in which a computing device is communicatively coupled to a sound processor of the cochlear implant system of FIG. 1 according to principles described herein.

FIG. 3 illustrates an exemplary configuration 300 in which a computing device 302 (e.g., a programming system or the like) is communicatively coupled (e.g., by way of a wired or wireless communication channel) to sound processor 104. Computing device 302 may be implemented by any suitable combination of physical computing and communication devices including, but not limited to, a fitting station or device, a programming device, a personal computer, a laptop computer, a handheld device, a mobile device (e.g., a mobile phone), a CPI device, and/or any other suitable component as may serve a particular implementation.

In some examples, computing device 302 may provide one or more user interfaces with which a user may interact. For example, a user interface may provide text, graphics, sounds, etc., to facilitate a successful insertion procedure of electrode lead 110 or effective programming of sound processor 104 as may serve a particular implementation. In some implementations, the user interface provided by computing device 302 may include a graphical user interface ("GUI") that allows a user (e.g., a surgeon, a person assisting the surgeon during an insertion procedure, a clinician, etc.) to direct computing device 302 to perform operations for locating a particular electrode 112 or for locating electrode lead 110 by, for example, locating all of electrodes 112-S with respect to the cochlea. After performing the electrode locating directed by the user, the GUI may provide information representative of the electrode location by way of visual or audible feedback as may serve a particular implementation.

Figure 4:
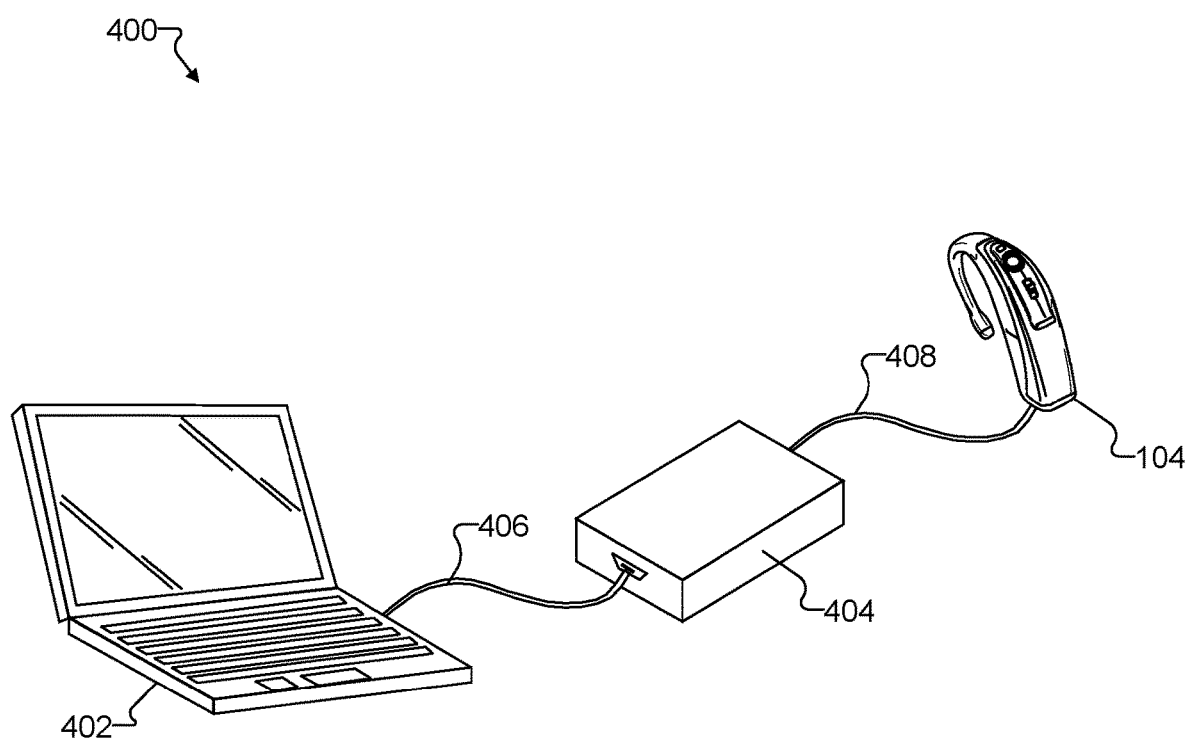
FIG. 4 illustrates an exemplary configuration in which the computing device of FIG. 3 is implemented by a personal computer and a clinician's programming interface device according to principles described herein.

FIG. 4 illustrates an exemplary configuration 400 in which computing device 302 is implemented by a personal computer 402 and a CPI device 404. As shown, personal computer 402 may be selectively and communicatively coupled to CPI device 404 by way of a cable 406. Likewise, CPI device 404 may be selectively and communicatively coupled to sound processor 104 by way of a cable 408. Cables 406 and 408 may each include any suitable type of cable that facilitates transmission of digital data between personal computer 402 and sound processor 104. For example, cable 406 may include a universal serial bus ("USB") cable and cable 408 may include any type of cable configured to connect to a programming port included in sound processor 104.

Figure 5:
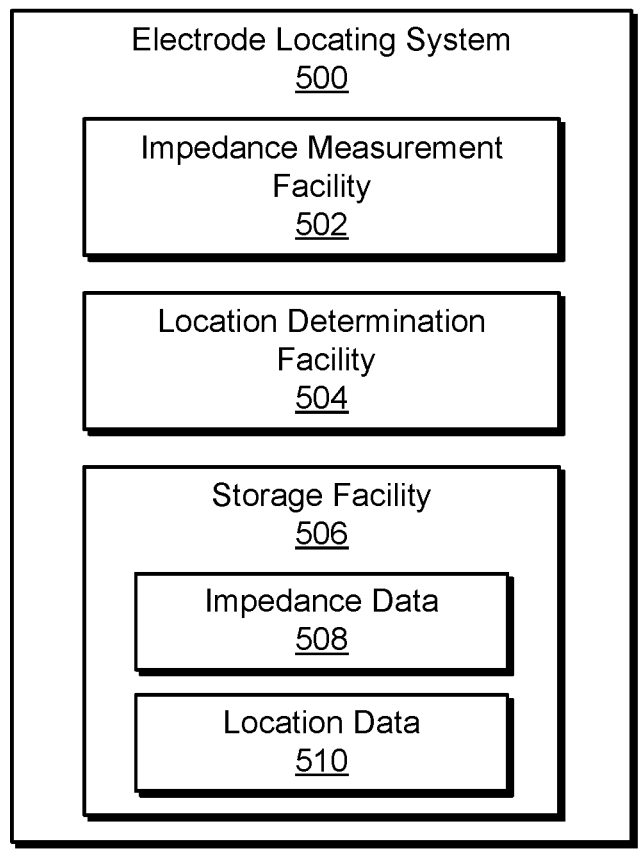
FIG. 5 illustrates a block diagram of exemplary components of an electrode locating system for use within a cochlear implant patient according to principles described herein.

FIG. 5 illustrates a block diagram of exemplary components of an electrode locating system 500 ("system 500"). System 500 may be configured to perform any of the operations described herein for locating electrodes and/or electrode leads within cochlear implant patients. To this end, as shown, system 500 may include an impedance measurement facility 502, a location determination facility 504, and a storage facility 506, which may be selectively and communicatively coupled to one another. It will be recognized that although facilities 502 through 506 are shown to be separate facilities in FIG. 5, facilities 502 through 506 may be combined into fewer facilities, such as into a single facility, or divided into more facilities as may serve a particular implementation. In some examples, system 500 may include, implement, or be implemented by a computing device such as computing device 302, described above. Each of facilities 502 through 506 will now be described in more detail.

Impedance measurement facility 502 may include or be implemented by one or more physical computing devices (e.g., including hardware and/or software such as processors, memories, communication interfaces, instructions stored in memory for execution by the processors, etc.) such as computing device 302, computing components included in sound processor 104, and/or other suitable computing devices that perform various operations associated with performing impedance measurements (e.g., excitation spread measurements) with respect to electrodes included in a cochlear implant system, or any combination thereof. As such, impedance measurement facility 502 may be configured to perform one or more excitation spread measurements by, for example, directing a first electrode (e.g., a stimulating electrode included in a plurality of electrodes disposed on an electrode lead included within a cochlear implant system) to generate an electrical pulse, and, in response to the generation of the electrical pulse, detecting a voltage between a second electrode and a reference (e.g., performing the voltage detection using a second electrode included within the plurality of electrodes and a reference such as a ground electrode that are both distinct from the first electrode). Impedance measurement facility 502 may perform excitation spread measurements for one electrode or, in certain examples, sequentially for all the stimulating electrodes included on an electrode lead. This may be done by way of various different possible configurations, as will be described in more detail below.

Location determination facility 504 may include or be implemented by one or more physical computing devices such as the same computing devices or similar (but separate) computing devices described above in relation to impedance measurement facility 502. Based on excitation spread measurements performed by impedance measurement facility 502, location determination facility 504 may be configured to determine whether at least one of the first electrode and the second electrode is located within the cochlea. Location determination facility 504 may perform this determination in any of the ways described herein. Moreover, as will be described in more detail below, by determining a location for each of the electrodes disposed on the distal portion of an electrode lead (e.g., electrodes 112-S in FIG. 1) location determination facility 504 may be configured to determine an insertion depth of the electrode lead within the cochlea.

In some examples, facilities 502 and 504 may perform the operations described above in real time during an insertion procedure (e.g., while the surgical insertion procedure is ongoing). As used herein, an operation is considered to be performed in "real time" when the operation is performed immediately and without undue delay (e.g., in real time or near real time). Accordingly, operations may be said to be performed in real time and users of system 500 may be considered to receive real time information during the insertion procedure even if the information is provided after a small delay (e.g., up to a few seconds).

Storage facility 506 may maintain impedance data 508, location data 510, and/or any other data received, generated, managed, maintained, used, and/or transmitted by facilities 502 through 504 in a particular implementation. Impedance data 508 may include data representative of impedance measurements (e.g., excitation spread measurements between different electrodes) that have been made, or data used to make such measurements (e.g., data representative of voltage or current levels for electrical pulses to be generated, data representative of timing information for detecting voltages in response to generated electrical pulses, etc.), or the like. Similarly, location data 510 may include data representative of electrodes that have been located, insertion depths of electrode leads that have been determined, or data to facilitate the determination of such data. Storage facility 506 may further include any other data as may serve a particular implementation of system 500 to facilitate performing one or more of the operations described herein.

Figure 6:
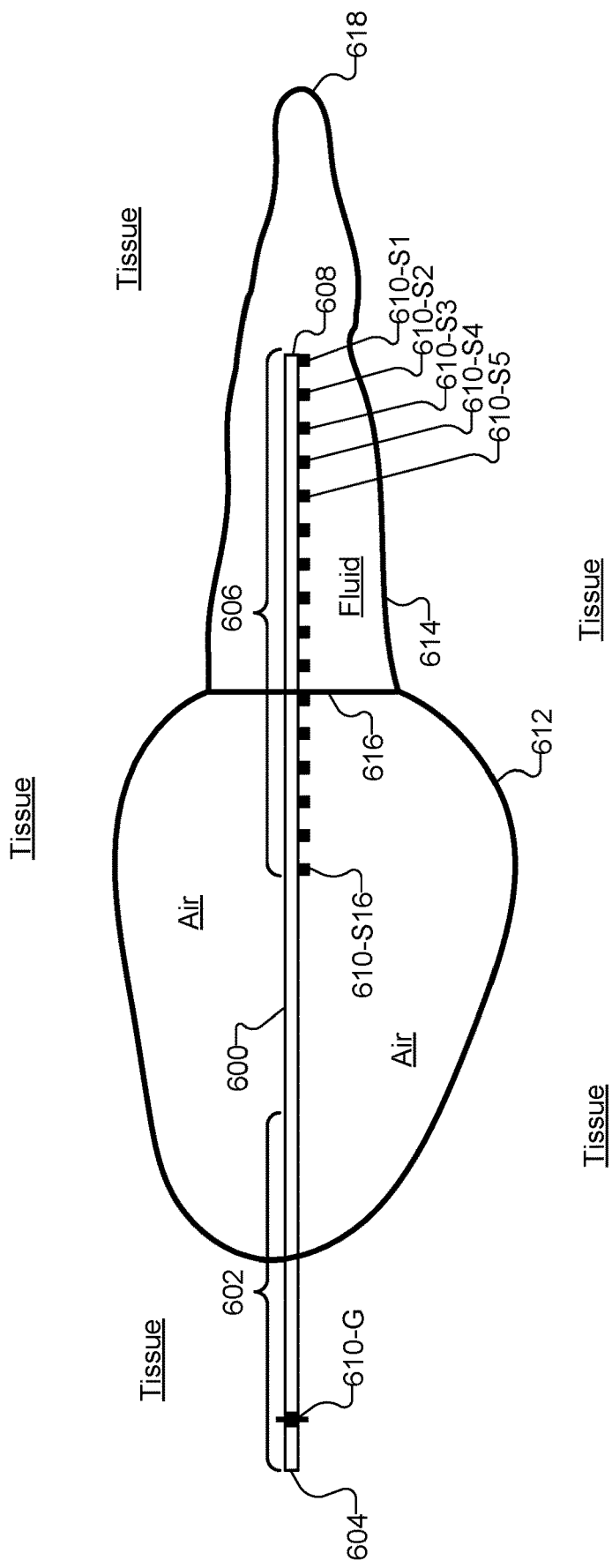
FIG. 6 illustrates exemplary aspects of an electrode lead and of patient anatomy as an insertion procedure is performed according to principles described herein.

FIG. 6 illustrates exemplary aspects of an electrode lead 600 and of patient anatomy as an insertion procedure is performed. Specifically, as shown, electrode lead 600 includes a proximal portion 602 beginning at a proximal end 604 and a distal portion 606 terminating at a distal end 608. Disposed on electrode lead 600 is a plurality of electrodes 610, including, on distal portion 606, a plurality of stimulating electrodes 610-S (e.g., stimulating electrodes 610-S1 through 610-S5 and 610-S16, which are explicitly labeled, and additional electrodes 610-S6 through 610-S15, which are not explicitly labeled in FIG. 6 but may be referred to herein), and including, on proximal portion 602, a ground electrode 610-G (e.g., a ring electrode).

FIG. 6 illustrates a particular position of electrode lead 600 during an insertion procedure in which electrode lead 600 (i.e., and proximal portion 606 in particular) is being inserted from a middle ear 612 of a patient into a cochlea 614 of the patient through a round window 616 associated with cochlea 614. For example, the goal of the insertion procedure may be to continue inserting distal portion 606 into cochlea 614 toward an apex 618 of cochlea 614 until the entirety of distal portion 606 (i.e., which may include all of electrodes 610-S) has passed through round window 616 to be located within cochlea 614.

In FIG. 6, various aspects of electrode lead 600 and the illustrated anatomical features of the patient are simplified for clarity of illustration. For instance, while cochlea 614 has been "unrolled" in FIG. 6, it will be understood that, as illustrated in FIG. 2, cochlea 614 has a curved, spiral-shaped structure and that electrode lead 600 curves to follow the spiral-shaped structure. Similarly, the anatomy of middle ear 612 and cochlea 614 omit many details and are not drawn to scale.

FIG. 6 does, however, illustrate at least one aspect of the patient's anatomy that allows electrode locating systems and methods described herein to function properly within the patient. As shown, on the cochlea side of round window 616, cochlea 614 contains conductive fluid ("fluid") that, unlike gaseous fluids (e.g., air) on the other side of round window 616, is conductive to electrical currents applied to the fluid. In certain examples, system 500 may distinguish between different fluids within cochlea 614 (e.g., perilymph in the scala vestibuli and scala tympani, endolymph in the scala media, etc.) based on different conductivities of the different fluids. In this way, system 500 may not only distinguish electrodes located in the fluid of cochlea 614 from electrodes still located in the air of middle ear 612, but may further distinguish between electrodes located in different parts of cochlea 614 (e.g., within one of the scala vestibuli or scala tympani, within the scala media, etc.).

The fluid within cochlea 614 may carry current and provide for current conduction paths for an electrical pulse (e.g., a pulse provided by a current source or voltage source) to spread to at least some extent between electrodes 610-S that have been inserted into cochlea 614 (i.e., that are surrounded by the fluid). Thus, for example, if an electrical pulse is generated at one particular electrode 610-S, such as 610-S1, the fluid may provide a conduction path from electrode 610-S1 to other electrodes 610-S that are included within cochlea 614 (i.e., electrodes 610-S2 through 610-S10 that are surrounded by the fluid at the moment illustrated in FIG. 6) and to tissue surrounding cochlea 614. The electrical pulse may be generated by a cochlear implant or other device communicatively coupled to proximal end 604. Thus, a return path for current associated with the electrical pulse may extend from electrode 610-S1, through the fluid of cochlea 614, through the tissue associated with cochlea 614 and middle ear 612, through ground electrode 610-G, back to the voltage or current source included on the cochlear implant or other device that generated the electrical pulse.

Because the fluid inside cochlea 614 may conduct current while air outside cochlea 614 (i.e., the air in middle ear 612 on the other side of round window 616) may not effectively conduct current, only electrodes 610-S that have passed through round window 616 into cochlea 614 and are surrounded by the fluid of cochlea 614 may be able to detect the excitation spread of the electrical pulse generated by electrode 610-S1 in the example above. Electrodes 610-S that have not yet been inserted through round window 616 (e.g., electrodes 610-S11 through 610-S16 at the moment illustrated by FIG. 6) may therefore not have a viable conduction path connecting them with electrode 610-S1, and may therefore not be able to detect the excitation spread of the electrical pulse generated at electrode 610-S1.

As described above an excitation spread measurement may be performed by, as in the example described above, generating an electrical pulse at a first electrode (e.g., electrode 610-S1 in the example above), and then detecting the electrical pulse (i.e., how the electrical pulse has spread) between a second electrode (e.g., one of electrodes 610-S2 through 610-S16 or 610-G) and a reference (e.g., ground electrode 610-G, a case ground of a cochlear implant, etc.). For example, the second electrode and the reference may both be separate from the first electrode, in contrast to how impedance measurements are typically performed. By knowing how much current or voltage was applied at the first electrode (e.g., by the current or voltage source that generates the electrical pulse) and how much current or voltage is detected at the second electrode, the extent to which the electrical pulse is able to spread between the first and second electrodes (e.g., through the fluid and/or tissue of cochlea 614) may be determined (e.g., using Ohm's Law and/or other similar principles). Accordingly, by detecting that the electrical pulse has spread to at least some extent from the first electrode to the second electrode by way of an excitation spread measurement involving an electrode known to be inserted into cochlea 614, system 500 may determine that both electrodes are inserted into cochlea 614. However, when an electrical pulse is determined to not have spread from the first electrode to the second electrode by way of an excitation spread measurement involving an electrode known to be inserted into cochlea 614 (i.e., when the electrical pulse cannot be detected at the second electrode because no conduction path exists between the first electrode and the second electrode due, for instance, to one of the electrodes being disposed in the air of middle ear 612), system 500 may determine that one of the electrodes has not yet entered into cochlea 614.

Moreover, by determining whether each of electrodes 610-S are located inside or outside cochlea 614 in this way, the insertion depth of the entire electrode lead 600 may be determined. For example, by determining that electrodes 610-S1 through 610-S10 are located within the fluid of cochlea 614 and that electrodes 610-S11 through 610-S16 are located within the air of middle ear 612, system 500 may determine that electrode lead 600 is a bit more than halfway into cochlea 614 but still needs to be inserted farther, as shown.

While the example above describes excitation spread measurements in which the electrical pulse is generated at an electrode known to already be inserted into cochlea 614 (i.e., electrode 610-S1), the same excitation spread measurement principles may also work if the electrode known to already be inserted into cochlea 614 (i.e., electrode 610-S1) is used to detect an electrical pulse generated at an electrode 610-S that is under test. For example, system 500 may determine whether electrode 610-S5, for instance, is located in cochlea 614 (i.e., whether electrode 610-S5 has a fluid conduction path with electrode 610-S1) either by generating the electrical pulse at electrode 610-S1 and attempting to detect the electrical pulse at electrode 610-S5, or vice versa, by generating the electrical pulse at electrode 610-S5 and attempting to detect the electrical pulse at electrode 610-S1. Accordingly, system 500 may include or have control over pulse generation and detection circuitry that is flexible to perform excitation spread measurements in these different ways.

Figure 7A:
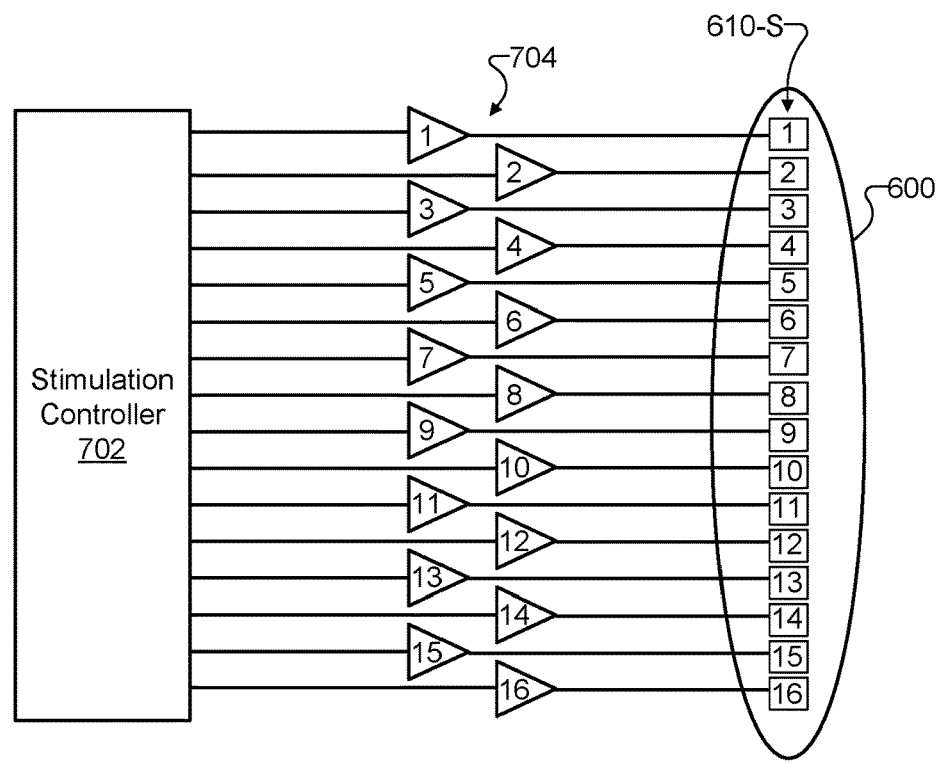
FIG. 7A illustrates exemplary aspects of how an electrical pulse may be generated on an electrode included on the electrode lead of FIG. 6 according to principles described herein.

To illustrate, FIG. 7A shows exemplary aspects of how an electrical pulse may be generated on an electrode included on electrode lead 600 in one implementation. Specifically, as shown, a stimulation controller 702 included within system 500 or included within a cochlear implant system (e.g., within a cochlear implant such as cochlear implant 108) that is under direction of system 500 may be configured to direct a particular driver 704 (i.e., one of drivers 704-1 through 704-16, labeled "1" through "16" under the "704" designation in FIG. 7A) to generate a pulse at any arbitrary electrode 610-S of electrode lead 600 (i.e., one of electrodes 610-S1 through 610-S16, labeled "1" through "16" under the "610-S" designation in FIG. 7A). For example, stimulation controller 702 may include logic for receiving instruction from impedance measurement facility 502 of system 500 to perform an excitation spread measurement and/or for directing, in response to the received instruction, at least one of drivers 704 to generate an electrical pulse at a respective at least one of electrodes 610-S. For instance, if impedance measurement facility 502 directs stimulation controller 702 to perform an excitation spread measurement involving electrode 610-S1, stimulation controller 702 may cause driver 704-1 (e.g., which may be implemented by a current source, a voltage source, or the like) to generate an electrical pulse at a particular time at electrode 610-S1.

Figure 7B:
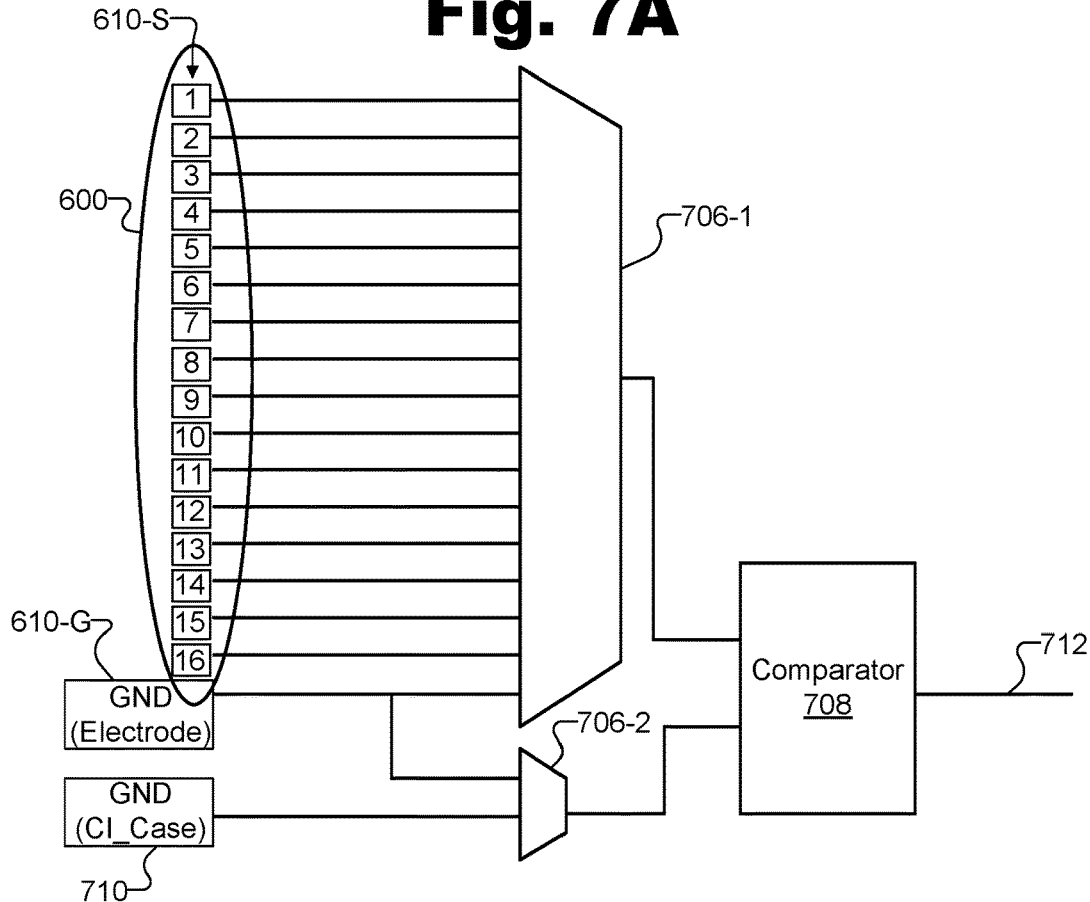
FIG. 7B illustrates exemplary aspects of how an electrical pulse may be detected at an electrode included on the electrode lead of FIG. 6 according to principles described herein.

Once an electrical pulse has been generated at one of electrodes 610-S, FIG. 7B illustrates exemplary aspects of how the electrical pulse may be detected at an electrode included on electrode lead 600 in one implementation. Just as system 500 may have flexibility to generate an electrical pulse at any arbitrary electrode as described above, the pulse detection circuitry illustrated in FIG. 7B may provide similar flexibility system 500 to be able to detect an electrical pulse at any electrode 612 on electrode lead 600 (e.g., including electrodes 610-S and ground electrode 610-G). To this end, as shown, the circuitry of FIG. 7B includes multiplexors 706 (e.g., multiplexors 706-1 and 706-2), which are configured to switch any of electrodes 610-S or 610-G into a first terminal of a comparator 708, and to switch either ground electrode 610-G or another suitable ground contact (e.g., a case ground 710 that is connected to ground electrode 610-G through some resistance such that the case ground may be at a different voltage than ground electrode 610-G) into a second terminal of comparator 708.

It will be understood that additional inputs may also be included in multiplexors 706 in certain implementations that are not shown in FIG. 7B. For example, all of the electrodes and grounds illustrated in FIG. 7B, as well as additional contacts, may be available as inputs to one or both of multiplexors 706 in certain implementations to provide for maximum flexibility. Multiplexors 706 may be under control of system 500 (e.g., impedance measurement facility 502 in particular) such that an appropriate electrode and an appropriate ground may be selected in order to attempt to detect an electrical pulse that has been generated at another electrode in an excitation spread measurement.

Comparator 708 may be implemented as a differential amplifier that generates a signal 712 representative of voltage difference between the signals input into comparator 708 (e.g., the voltage difference between an electrode 610 selected in multiplexor 706-1 and a ground selected in multiplexor 706-2). For example, as will be described in more detail below, comparator 708 may output (i.e., as signal 712) a voltage between one of stimulating electrodes 610-S and ground electrode 610-G, or a voltage between ground electrode 610-G and case ground 710. Case ground 710 may be a case ground provided by a housing of the cochlear implant or other device in which stimulation controller 702, drivers 704, multiplexors 706, and comparator 708 are housed. As mentioned above, case ground 710 may be coupled to other grounds contacts such as ground electrode 610-G through a resistor such that a voltage may exist between ground electrode 610-G and case ground 710 that may be detected by comparator 708.

Figure 8A:
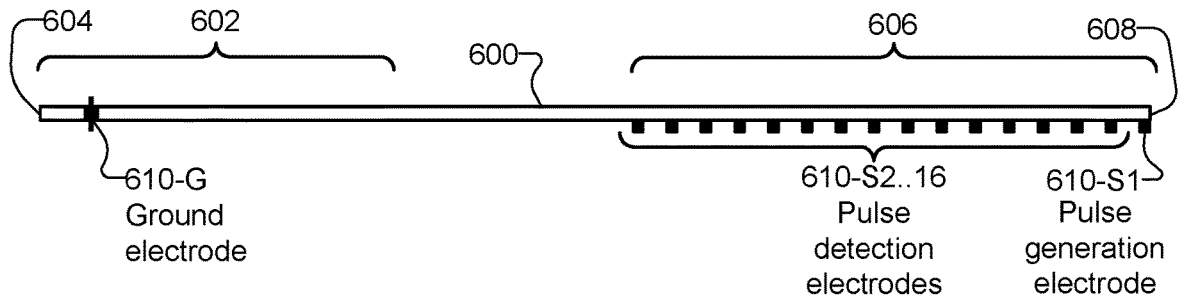
FIG. 8A illustrates how each electrode on the electrode lead of FIG. 6 is used to perform electrode locating within a cochlear implant patient in a first exemplary implementation according to principles described herein.
Figure 8B:
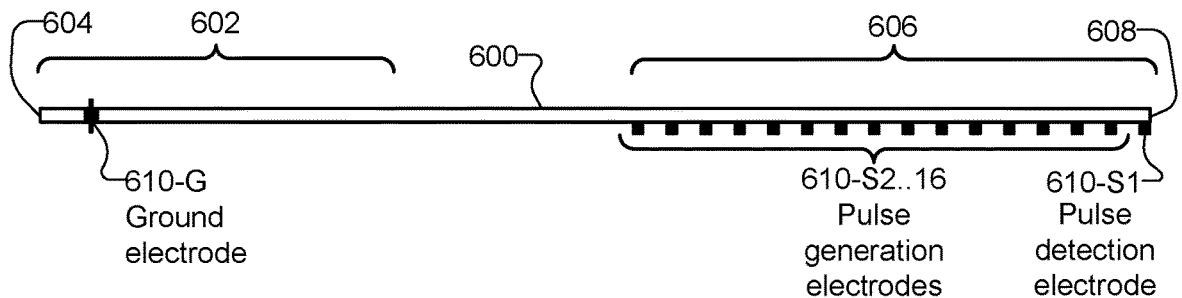
FIG. 8B illustrates how each electrode on the electrode lead of FIG. 6 is used to perform electrode locating within a cochlear implant patient in a second exemplary implementation according to principles described herein.
Figure 8C:
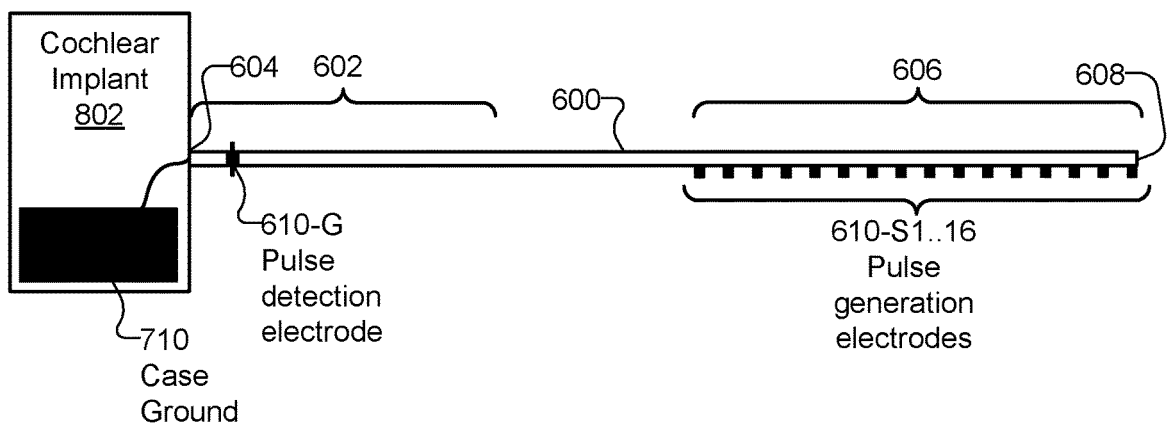
FIG. 8C illustrates how each electrode on the electrode lead of FIG. 6 is used to perform electrode locating within a cochlear implant patient in a third exemplary implementation according to principles described herein.

As mentioned above, if system 500 includes or has control over flexible pulse generation and detection circuitry such as shown in FIGS. 7A and 7B, system 500 may perform electrode locating operations within a cochlear implant patient in various different ways. FIGS. 8A through 8C illustrate a few possible such implementations for locating individual electrodes with respect to a cochlea such as cochlea 614 and/or for determining an insertion depth for electrode lead 600 with respect to the cochlea (e.g., by locating each of the individual stimulating electrodes 610-S disposed on electrode lead 600).

First, FIG. 8A illustrates how each electrode on electrode lead 600 is used to perform electrode locating within a cochlear implant patient in a first exemplary implementation. As shown in the implementation of FIG. 8A, the electrode 610-S nearest to distal end 608 of electrode lead 600 (i.e., the first electrode to enter the cochlea, electrode 610-S1 in the example of FIG. 8A) is the electrode that generates the electrical pulse, and, as such, system 500 performs the excitation spread measurement (e.g., directs the electrical pulse to be generated at electrode 610-S1) when the electrode is located within the cochlea and a reference (e.g., ground electrode 610-G or the like) is external to the cochlea. System 500 may then determine whether each of the other stimulating electrodes (e.g., electrodes 610-S2 through 610-S16) is also located within the cochlea by determining whether a voltage detected at each of the electrodes exceeds a predetermined threshold.

Specifically, the predetermined threshold may be set at a non-zero value and configured such that, if the detected voltage at each of the pulse detection electrodes 610-S2 through 610-S16 (i.e., the detected voltage between each of the pulse detection electrodes 610-S2 through 610-S16 and a reference such as ground electrode 610-G) exceeds the predetermined threshold, system 500 (e.g., location determination facility 504 in particular) may determine that the pulse detection electrodes are located within the cochlea because a fluid conduction path exists between pulse generation electrode 610-S1 and the respective pulse detection electrode that allows for a voltage larger than the predetermined threshold to be detected. Conversely, if the detected voltage at each of pulse detection electrodes 610-S2 through 610-S16 does not exceed the predetermined threshold, system 500 may determine that the pulse detection electrodes are not located within the cochlea (e.g., because the fluid conduction path does not exist between pulse generation electrode 610-S1 and the respective pulse detection electrodes to allow for a non-zero voltage larger than the predetermined threshold to be detected).

In some examples using the implementation of FIG. 8A, one or more particular electrodes (e.g., one of pulse detection electrodes 610-S2 through 610-S16) may be located by performing one or more excitation spread measurements and corresponding location determination operations based on the excitation spread measurements in a piecemeal fashion. In other examples, a sequence of excitation spread measurements (e.g., including excitation spread measurements for each of the pulse detection electrodes under test) may be performed in order to determine an insertion depth of electrode lead 600 with respect to the cochlea. In other words, system 500 may determine whether each of electrodes 610-S is located within the cochlea by using each of electrodes 610-S other than electrode 610-S1 as a pulse detection electrode in an excitation spread measurement in the sequence of excitation spread measurements (e.g., an excitation spread measurement performed as described above for one electrode). In certain implementations, the excitation spread measurements may alternatively be performed concurrently or simultaneously with one another, rather than one at a time in sequence.

Next, FIG. 8B illustrates how each electrode on electrode lead 600 is used to perform electrode locating within a cochlear implant patient in a second exemplary implementation. As shown in the implementation of FIG. 8B, the electrode 610-S nearest to distal end 608 of electrode lead 600 (i.e., the first electrode to enter the cochlea, electrode 610-S1 in the example of FIG. 8B) is now the electrode that attempts to detect electrical pulses generated when system 500 performs the excitation spread measurement when the electrode is located within the cochlea and the reference (e.g., ground electrode 610-G) is external to the cochlea. Each of the other electrodes 610-S may now be configured to generate respective electrical pulses in respective excitation spread measurements. Thus, in this case, system 500 may determine whether each of the other stimulating electrodes (e.g., electrodes 610-S2 through 610-S16) is also located within the cochlea with electrode 610-S1 by determining whether a voltage detected at electrode 610-S1 exceeds a predetermined threshold such as the predetermined threshold described above in relation to FIG. 8A.

Specifically, the predetermined threshold may be set at a non-zero value and configured such that, if the voltage detected at pulse detection electrode 610-S1 for each of the electrical pulses generated at pulse generation electrodes 610-S2 through 610-S16 (i.e., the voltage detected between pulse detection electrode 610-S1 and a reference such as ground electrode 610-G) exceeds the predetermined threshold, system 500 (e.g., location determination facility 504 in particular) may determine that the pulse generation electrodes are located within the cochlea (e.g., because a fluid conduction path exists between pulse detection electrode 610-S1 and the respective pulse generation electrode that allows for a voltage larger than the predetermined threshold to be detected). Conversely, if the detected voltage at electrode 610-S1 for each of the electrical pulses generated at pulse generation electrodes 610-S2 through 610-S16 does not exceed the predetermined threshold, system 500 may determine that the pulse generation electrodes are not located within the cochlea (e.g., because the fluid conduction path does not exist between pulse detection electrode 610-S1 and the respective pulse generation electrodes to allow for a non-zero voltage larger than the predetermined threshold to be detected).

In some examples using the implementation of FIG. 8B, one or more particular electrodes (e.g., one of pulse generation electrodes 610-S2 through 610-S16) may be located by performing one or more excitation spread measurements and corresponding location determination operations in a piecemeal fashion. In other examples, a sequence of excitation spread measurements (e.g., including excitation spread measurements for each of the pulse generation electrodes under test) may be performed in order to determine an insertion depth of electrode lead 600 with respect to the cochlea. In other words, system 500 may determine whether each of electrodes 610-S is located within the cochlea by using each of electrodes 610-S other than electrode 610-S1 as a pulse generation electrode in an excitation spread measurement in the sequence of excitation spread measurements (e.g., an excitation spread measurement performed as described above for one electrode).

FIG. 8C illustrates how each electrode on electrode lead 600 may be used to perform electrode locating within a cochlear implant patient in a third exemplary implementation. The excitation spread measurements of the third implementation illustrated by FIG. 8C is slightly different from the implementations illustrated by FIGS. 8A and 8B, in that no stimulating electrode 610-S is used as a pulse detection electrode such that no conduction path through the fluid of the cochlea alone is detected, as was done with the other implementations. In some cases, the third implementation illustrated by FIG. 8C may thus be less prone to "false positives" that may occur when an electrode at or near the round window may have a tenuous or weak fluid conduction path with the other electrodes (e.g., based on trace amounts of fluid that may emerge from the cochlea when the round window is traversed by electrode lead 600). For example, referring to FIG. 6, electrode 610-S11 is shown to be just outside round window 616, and thus should not be detected as being located within cochlea 614. However, in some examples, tissue of round window 616 and/or fluid spilling out of cochlea 614 around an entrance of electrode lead 600 may provide a conduction path between electrode 610-S1 and 610-S11 that may cause a "false positive" indicating that electrode 610-S11 is located inside cochlea 614, rather than just outside cochlea 614.

Returning to FIG. 8C, the third implementation may be less prone to such false positive measurements. As shown in the implementation of FIG. 8C, any or all of stimulating electrodes 610-S (e.g., electrodes 610-S1 through 610-S16) may be used as a pulse generation electrode in an excitation spread measurement, while the pulse detection electrode for each excitation spread measurement may be ground electrode 610-G. As described above, when one of electrodes 610-S is used as a pulse detection electrode (e.g., in the implementations of FIGS. 8A and 8B), ground electrode 610-G may be used as the reference with respect to which the voltage of the pulse detection electrode is measured. However, when ground electrode 610-G is used as the pulse detection electrode (e.g., in the implementation of FIG. 8C), case ground 710 (i.e., the case ground of a cochlear implant 802 that includes the pulse generation and detection circuitry described above in FIGS. 7A and 7B) may be used as the reference with respect to which the voltage of pulse detection electrode 610-G is measured.

This implementation operates in spite of the fact that ground electrode 610-G is disposed on proximal portion 602 of electrode lead 600 and is configured to remain external to the cochlea even after distal portion 606 of electrode lead 600 has been fully inserted into the cochlea (i.e., meaning that no conduction path based solely on fluid of the cochlea with ever be established between ground electrode 610-G and any of the pulse generation electrodes 610-S. In this implementation, system 500 may determine whether each of the pulse generation electrodes 610-S is located within the cochlea based on whether the detected voltage at pulse detection electrode 610-G (e.g., the detected voltage between ground electrode 610-G and a case ground of the cochlear implant, for example) exceeds a predetermined threshold configured similarly to other predetermined thresholds described above. Specifically, if the detected voltage at ground electrode 610-G exceeds the predetermined threshold, system 500 (e.g., location determination facility 504 in particular) may determine that the respective pulse generation electrode 610-S is located within the cochlea, while, if the detected voltage at ground electrode 610-G does not exceed the predetermined threshold, system 500 may determine that the respective pulse generation electrode 610-S is not located within the cochlea.

As with the other implementations described above, in some examples using the implementation of FIG. 8C, one or more particular electrodes (e.g., one of pulse generation electrodes 610-S1 through 610-S16) may be located by performing one or more excitation spread measurements and corresponding location determination operations based on the excitation spread measurements in a piecemeal fashion. In other examples, a sequence of excitation spread measurements (e.g., including excitation spread measurements for each of the pulse generation electrodes under test) may be performed in order to determine an insertion depth of electrode lead 600 with respect to the cochlea. In other words, system 500 may determine whether each of electrodes 610-S is located within the cochlea by using each of electrodes 610-S as a pulse generation electrode in an excitation spread measurement in the sequence of excitation spread measurements (e.g., an excitation spread measurement performed as described above for one electrode).

As has been mentioned, electrode locating systems and methods described herein may allow a user (e.g., a surgeon, a person otherwise facilitating an insertion procedure, a clinician, etc.) to query and find out whether one or more particular electrodes are located within the cochlea. For example, system 500 may provide a user interface (e.g., a GUI) for use by a user associated with system 500 and provide (e.g., to the user by way of the user interface) information representative of the determination whether the particular electrodes are located within the cochlea. For example, the user interface may present this information by way of a graphic, an icon, a textual explanation, a particular color (e.g., green for electrodes located within the cochlea, red for electrodes located external to the cochlea, etc.), a graph (e.g., a voltage graph showing the voltage detected by the pulse detection electrode in a particular excitation spread measurement), a sound, or by any other output as may serve a particular implementation.

As further mentioned above, electrode locating systems and methods described herein may also perform sequences of excitation spread measurements that involve all of the electrodes disposed on the distal portion of the electrode lead (i.e., all of electrodes 610-S). For example, based on a sequence of excitation spread measurements, system 500 may determine whether each of the electrodes disposed on the distal portion of the electrode lead is located within the cochlea, and, based on that determination, may determine an insertion depth of the electrode lead within the cochlea. As such, along with the user interface for providing information about particular electrodes, system 500 may further provide a user interface for use by the user by way of which system 500 provides information to the user representative of the determined insertion depth of the electrode lead within the cochlea.

The information representative of the insertion depth may be expressed in any of the ways described above, as well as in other way as may be convenient and helpful to the user. For example, the insertion depth may be expressed as a percentage of the total distal portion of the electrode lead that has already been inserted into the cochlea (e.g., the insertion depth of the electrode lead is at 40%), as a percentage or number of electrodes that have already been inserted with respect to a total number of electrodes that are to be inserted (e.g., 5 out of 16 electrodes have been inserted, 31% of the electrodes have been inserted, etc.), or in another way that facilitates the user in conveniently and easily understanding what the current location of the electrode lead is with respect to the cochlea.

Moreover, by continuously monitoring and/or tracking the insertion depth of the electrode, system 500 (e.g., software included within system 500 that implements or is otherwise associated with the user interface) may also perform other useful operations. For example, system 500 may receive other types of information (e.g., from other types of detection systems integrated within system 500 or other associated systems operating with the cochlear implant system that are not explicitly described herein) that system 500 may correlate with electrode lead insertion depth information to provide users with additional helpful insights. For instance, in real time during an insertion procedure (e.g., while the electrode lead is at a determined insertion depth within the cochlea), system 500 may detect (e.g., by way of another integrated detection system), an occurrence of an event associated with the insertion procedure. The event may be any suitable type of event that may occur and be detected during the insertion procedure such as a trauma event in which it is detected that the electrode lead has caused trauma to the cochlea. Specifically, for instance, the event may be a translocation event in which it is detected that the electrode lead has translocated from one scala of the cochlea (e.g., the scala tympani) to another scala of the cochlea (e.g., the scala vestibuli), a basilar membrane event in which it is detected that the electrode lead has caused trauma to the basilar membrane and/or hair cells or auditory nerves associated with the membrane (e.g., by touching and damaging the membrane during the insertion procedure or the like), or any other event as may be relevant to a particular implementation.

In response to the detection of the occurrence of the event, and equipped with the information about the determined insertion depth of the electrode lead, system 500 may store (e.g., in a storage facility associated with system 500 such as storage facility 506) a record representative of the occurrence of the event and the determined insertion depth of the electrode lead within the cochlea. For example, system 500 may store a record that indicates that a translocation trauma event occurred to the patient's cochlea when the electrode lead had been inserted up to, for instance, the seventh electrode. Even if the event may not be reversed (e.g., even if trauma that has been invoked cannot be fixed), system 500 may use such stored records to improve future insertion procedures. For example, system 500 may use the stored record representative of the occurrence of the event and the determined insertion depth of the electrode lead within the cochlea to facilitate a subsequent insertion procedure of another electrode lead into a cochlea of another patient. For instance, system 500 may indicate to the surgeon or a person assisting the surgeon that a particular part of the insertion procedure is approaching where trauma has occurred in past insertion procedures. As a result, the surgeon may slow down and/or otherwise perform this part of the insertion procedure with particular care to try to avoid the trauma that has occurred in the previous insertion procedures.

Regardless of how a user interface provided by system 500 displays information about electrode locations or electrode lead insertion depths, the data from which the information output to the user is derived may be illustrated as a detected voltage signal that corresponds to one or more electrodes and either exceeds or does not exceed a predetermined voltage threshold, as described above. To illustrate, FIGS. 9A and 9B show different insertion depths of electrode lead 600 with respect to cochlea 614 at different moments during an insertion procedure, as well as resulting voltages graphs from a sequence of excitation spread measurements performed at those moments.

Figure 9A:
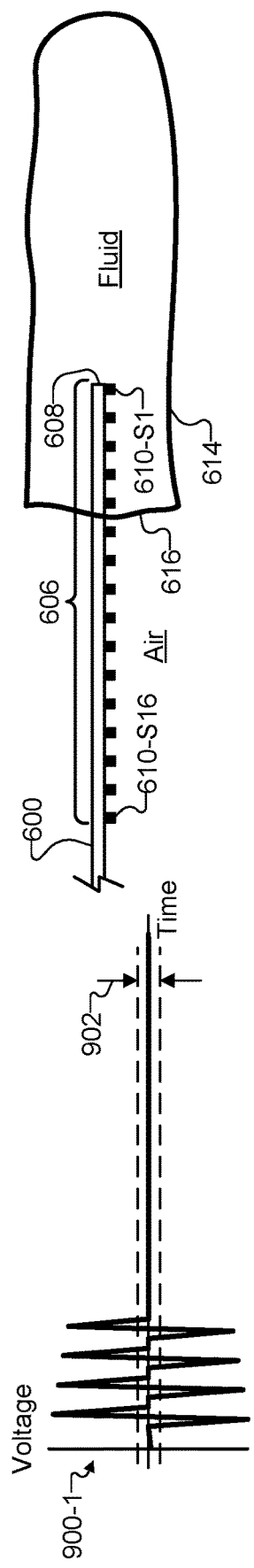
FIG. 9A illustrates exemplary results of a sequence of excitation spread measurements performed at a first point in time during an insertion procedure of the electrode lead of FIG. 6 into a cochlea of a patient according to principles described herein.
Figure 9B:
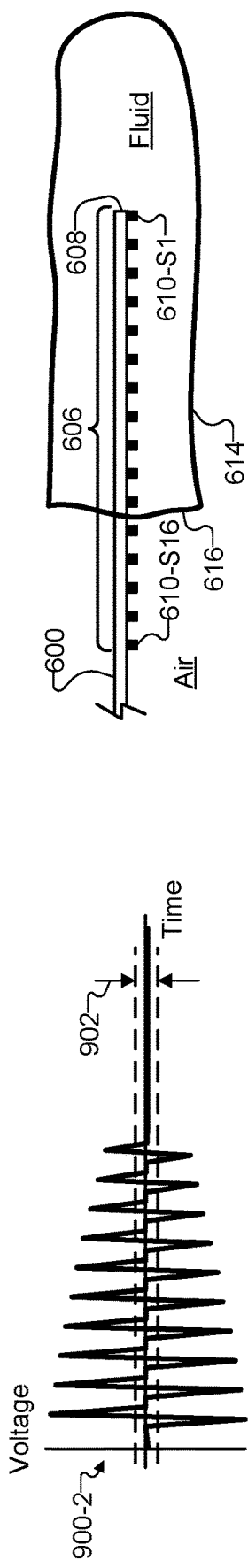
FIG. 9B illustrates exemplary results of another sequence of excitation spread measurements performed at a second point in time during the insertion procedure of the electrode lead of FIG. 6 into the cochlea of the patient according to principles described herein.

Specifically, FIG. 9A illustrates exemplary results of a sequence of excitation spread measurements performed at a first point in time during an insertion procedure of electrode lead 600 into cochlea 614 of the patient, while FIG. 9B illustrates exemplary results of another sequence of excitation spread measurements performed at a second point in time during the insertion procedure of electrode lead 600 into cochlea 614. In these moments (i.e., at the first and second points in time illustrated by FIGS. 9A and 9B), system 500 may perform excitation spread measurements and determine whether electrodes are located within cochlea 614 in real time during the insertion procedure when the distal portion of electrode lead 600 is being inserted into the cochlea (e.g., while the distal portion is in motion or is momentarily still during the procedure so that a measurement may be taken).

Figure 9C:
FIG. 9C illustrates exemplary results of yet another sequence of excitation spread measurements performed at a point in time subsequent to the completion of the insertion procedure of the electrode lead of FIG. 6 into the cochlea of the patient according to principles described herein.

FIG. 9C illustrates exemplary results of yet another sequence of excitation spread measurements performed at a point in time after the completion of the insertion procedure of electrode lead 600 into the cochlea of the patient. For example, FIG. 9C may be associated with a moment right at the end of the insertion procedure, or at any moment subsequent to the insertion procedure (e.g., at a later visit of the patient to a clinician). In this moment (i.e., at the point in time illustrated by FIG. 9C), system 500 may perform excitation spread measurements and determine whether electrodes are located within cochlea 614 subsequent to the insertion procedure (e.g., without regard to real time) when the distal portion of the electrode lead has been inserted into the cochlea and is stationary with respect to the cochlea.

Included in each of FIGS. 9A through 9C is a respective voltage vs. time graph 900 (e.g., graphs 900-1 in FIG. 9A at the first point in time, 900-2 in FIG. 9B at the second point in time, and 900-3 in FIG. 9C at the subsequent point in time when the insertion procedure is complete). Each of graphs 900 illustrate voltages that may be detected during a full sequence of excitation spread measurements (e.g., a sequence of excitation spread measurements in which locations for every stimulating electrode 610-S is determined). For example, graphs 900 may represent signal 712 in FIG. 7 for any of the implementations illustrated in FIG. 8. It will be understood that, while voltage values and times may be different from one implementation to another, any of the implementations illustrated in FIG. 8 may produce any of graphs 900 or graphs similar to them. For example, graphs generated by the third implementation may be similar to graphs 900 but different in that an additional pulse corresponding to electrode 610-S1 may be included with the other pulses representing other electrodes 610-S that are located within cochlea 614, and the tapering off of the magnitudes of the pulses may look different (e.g., may be non-existent or less pronounced).

As shown, each of graphs 900 include a number of voltage pulses corresponding to the number of electrodes located within cochlea 614 other than the first electrode that is already known to be located within cochlea 614 (i.e., electrode 610-S1). In other words, each graph includes a voltage pulse (i.e., a voltage that exceeds a predetermined threshold 902) for each electrode that has a fluid conduction path with electrode 610-S1, and includes no voltage pulse (i.e., the voltage stays below predetermined threshold 902) for each electrode that does not have a conduction path with electrode 610-S1. For example, in graph 900-1, exactly four pulses are shown because exactly four other electrodes are currently located with electrode 610-S1 in cochlea 614 at the point in time illustrated by FIG. 9A. It will be understood that the four pulses do not necessarily indicate that only four excitation spread measurements were made. Rather, the four pulses indicate that, while excitation spread measurements have been made for each of electrodes 610-S2 through 610-S16, threshold-exceeding voltages were only detected for the excitation spread measurements associated with electrodes 610-S2 through 610-S5 (i.e., the electrodes located within cochlea 614).

As another example, in graph 900-2, exactly ten pulses are shown because exactly ten other electrodes are currently located with electrode 610-S1 in cochlea 614 at the point in time illustrated by FIG. 9B. Similarly, in graph 900-3, fifteen pulses are shown corresponding to each of electrodes 610-S2 through 610-S16 because all of electrodes 610-S are located within cochlea 614 as the insertion procedure is complete. As mentioned above, if the third implementation illustrated by FIG. 8C where employed, graphs 900-1 through 900-3 may further include a fifth, an eleventh, and a sixteenth pulse, respectively, corresponding to an excitation spread measurement between electrodes 610-S1 and 610-G.

As shown in graphs 900-1 through 900-3, each pulse may taper off slightly as compared to the pulse before it. This is because the impedance between electrode 610-S1 and each subsequent electrode (e.g., electrodes 610-S2, 610-S3, and so forth) becomes slightly greater as the distance between the electrodes increases, causing the detected voltage to drop off. However, as shown in graph 900-3, predetermined threshold 902 may be low enough that a pulse corresponding even to the final electrode to be inserted into cochlea 614 (i.e., electrode 610-S16) may be greater than predetermined threshold 902.

Figure 10:
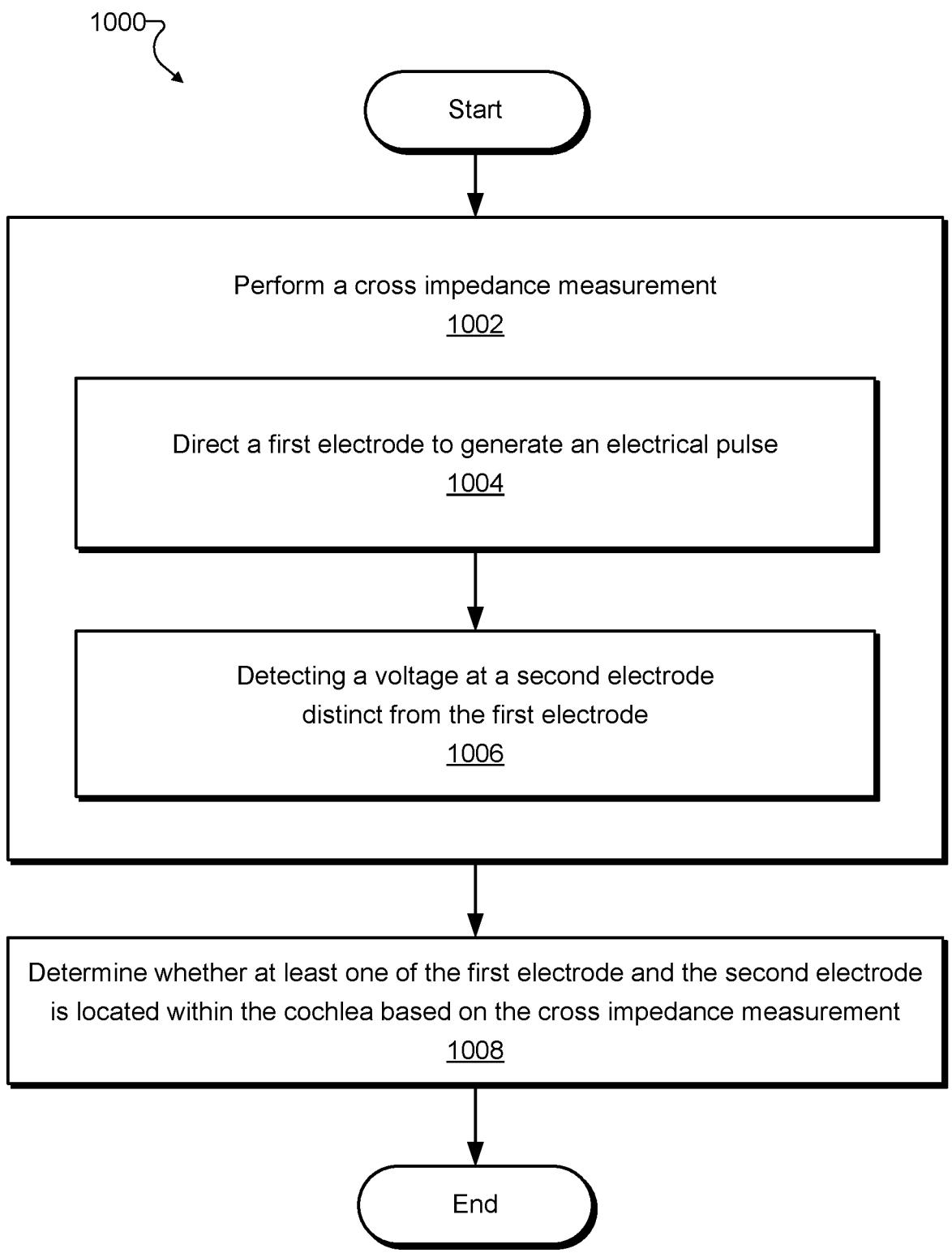
FIG. 10 illustrates an exemplary electrode locating method for use within a cochlear implant patient according to principles described herein.

FIG. 10 illustrates an exemplary electrode locating method 1000 for use within a cochlear implant patient. One or more of the operations shown in FIG. 10 may be performed by electrode locating system 500 and/or any implementation thereof. While FIG. 10 illustrates exemplary operations according to one embodiment, other embodiments may omit, add to, reorder, and/or modify any of the operations shown in FIG. 10.

In operation 1002, an electrode locating system associated with (e.g., communicatively coupled with, integrated by, etc.) a cochlear implant system may perform an excitation spread measurement. Operation 1002 may be performed in any of the ways described herein. For instance, operation 1002 may be performed by performing operations 1004 and 1006, which will be described now.

In operation 1004, the electrode locating system may direct a first electrode to generate an electrical pulse. For instance, the first electrode may be included in a plurality of electrodes disposed on an electrode lead included within the cochlear implant system. The electrode may comprise a proximal portion configured to be coupled with a cochlear implant (e.g., a cochlear implant included within the cochlear implant system), as well as a distal portion configured to be inserted into a cochlea of a patient by way of an insertion procedure. Operation 1004 may be performed in any of the ways described herein.

In operation 1006, the electrode locating system may detect a voltage in response to the generation of the electrical pulse in operation 1004. For example, the electrical stimulation may detect the voltage between a second electrode included within the plurality of electrodes and a reference. The second electrode and the reference may both be distinct from the first electrode. Operation 1006 may be performed in any of the ways described herein. When operation 1006 has been performed, operation 1002 may be complete such that method 1000 may proceed to operation 1008.

In operation 1008, the electrode locating system may determine whether at least one of the first electrode and the second electrode is located within the cochlea. For example, the electrode locating system may determine whether the at least one of the first electrode and the second electrode is located within the cochlea based on the excitation spread measurement performed in operation 1002 (i.e., by way of operations 1004 and 1006). Operation 1008 may be performed in any of the ways described herein.

In certain embodiments, one or more of the processes described herein may be implemented at least in part as instructions embodied in a non-transitory computer-readable medium and executable by one or more computing devices. In general, a processor (e.g., a microprocessor) receives instructions, from a non-transitory computer-readable medium (e.g., a memory, etc.) and executes the instructions, thereby performing one or more processes, including one or more of the processes described herein. Such instructions may be stored and/or transmitted using any of a variety of known computer-readable media.

A computer-readable medium (also referred to as a processor-readable medium) includes any non-transitory medium that participates in providing data (e.g., instructions) that may be read by a computer (e.g., by a processor of a computer). Such a medium may take many forms, including, but not limited to, non-volatile media, and/or volatile media. Non-volatile media may include, for example, optical or magnetic disks and other persistent memory. Volatile media may include, for example, dynamic random access memory ("DRAM"), which typically constitutes a main memory. Common forms of computer-readable media include, for example, a disk, hard disk, magnetic tape, any other magnetic medium, a compact disc read-only memory ("CD-ROM"), a digital video disc ("DVD"), any other optical medium, random access memory ("RAM"), programmable read-only memory ("PROM"), erasable programmable read-only memory ("EPROM"), electrically erasable programmable read-only memory ("EEPROM"), a Flash EEPROM device, any other memory chip or cartridge, or any other tangible medium from which a computer can read.

Figure 11:
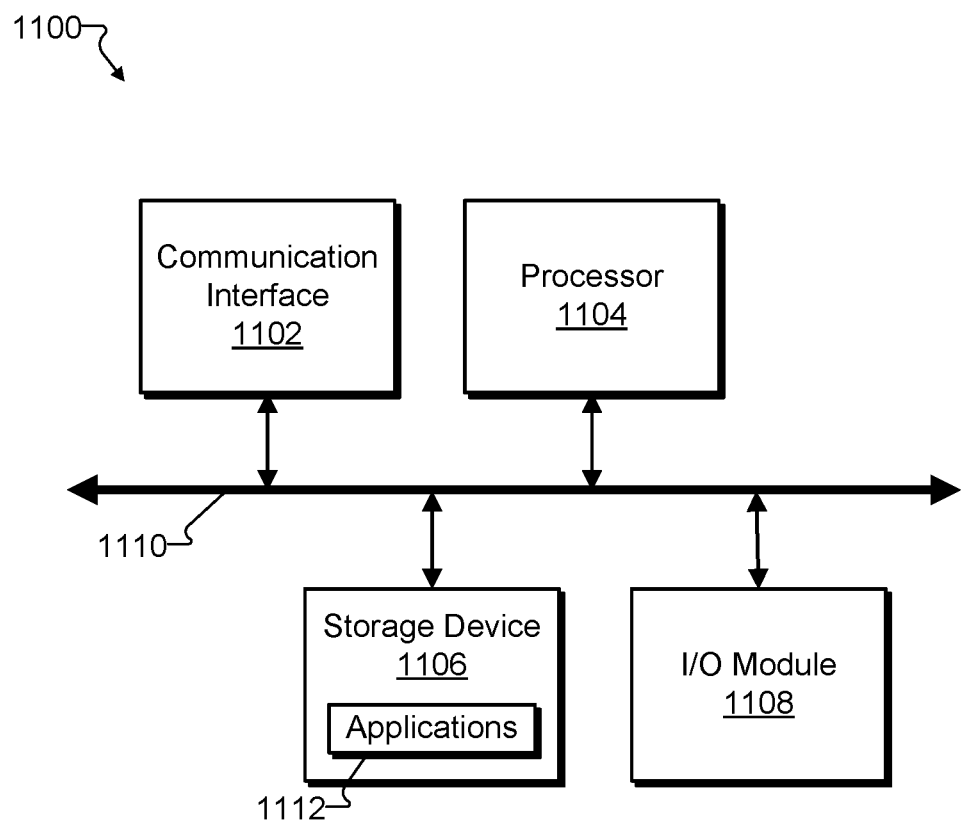
FIG. 11 illustrates an exemplary computing device according to principles described herein.

FIG. 11 illustrates an exemplary computing device 1100 that may be specifically configured to perform one or more of the processes described herein. As shown in FIG. 11, computing device 1100 may include a communication interface 1102, a processor 1104, a storage device 1106, and an input/output ("I/O") module 1108 communicatively connected via a communication infrastructure 1110. While an exemplary computing device 1100 is shown in FIG. 11, the components illustrated in FIG. 11 are not intended to be limiting. Additional or alternative components may be used in other embodiments. Components of computing device 1100 shown in FIG. 11 will now be described in additional detail.

Communication interface 1102 may be configured to communicate with one or more computing devices. Examples of communication interface 1102 include, without limitation, a wired network interface (such as a network interface card), a wireless network interface (such as a wireless network interface card), a modem, an audio/video connection, and any other suitable interface.

Processor 1104 generally represents any type or form of processing unit capable of processing data or interpreting, executing, and/or directing execution of one or more of the instructions, processes, and/or operations described herein. Processor 1104 may direct execution of operations in accordance with one or more applications 1112 or other computer-executable instructions such as may be stored in storage device 1106 or another computer-readable medium.

Storage device 1106 may include one or more data storage media, devices, or configurations and may employ any type, form, and combination of data storage media and/or device. For example, storage device 1106 may include, but is not limited to, a hard drive, network drive, flash drive, magnetic disc, optical disc, RAM, dynamic RAM, other non-volatile and/or volatile data storage units, or a combination or sub-combination thereof. Electronic data, including data described herein, may be temporarily and/or permanently stored in storage device 1106. For example, data representative of one or more executable applications 1112 configured to direct processor 1104 to perform any of the operations described herein may be stored within storage device 1106. In some examples, data may be arranged in one or more databases residing within storage device 1106.

I/O module 1108 may be configured to receive user input and provide user output and may include any hardware, firmware, software, or combination thereof supportive of input and output capabilities. For example, I/O module 1108 may include hardware and/or software for capturing user input, including, but not limited to, a keyboard or keypad, a touch screen component (e.g., touch screen display), a receiver (e.g., an RF or infrared receiver), and/or one or more input buttons.

I/O module 1108 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1108 is configured to provide graphical data to a display for presentation to a user. The graphical data may be representative of one or more graphical user interfaces and/or any other graphical content as may serve a particular implementation.

In some examples, any of the facilities or systems described herein may be implemented by or within one or more components of computing device 1100. For example, one or more applications 1112 residing within storage device 1106 may be configured to direct processor 1104 to perform one or more processes or functions associated with impedance measurement facility 502 or location determination facility 504 within system 500. Likewise, storage facility 506 within system 500 may be implemented by or within storage device 1106.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:
1. A system comprising:
a memory storing instructions; and
a processor communicatively coupled to the memory and configured to execute the instructions to:
perform an excitation spread measurement during an insertion procedure that is being performed to insert a plurality of electrodes disposed on an electrode lead into a cochlea of a patient, the excitation spread measurement including:
directing a first electrode of the plurality of electrodes to generate an electrical pulse at a particular time during the insertion procedure when the first electrode has already been inserted into the cochlea and, in response to the generation of the electrical pulse by the first electrode, detecting a voltage between a second electrode of the plurality of electrodes that has not yet been inserted into the cochlea and a ground contact that is to remain external to the cochlea after the insertion procedure; and determine, based on the excitation spread measurement, that the second electrode has not yet been inserted into the cochlea at the particular time.

2. The system of claim 1, wherein the performing of the excitation spread measurement and the determining that the second electrode has not yet been inserted into the cochlea are performed in real time during the insertion procedure.

3. The system of claim 1, wherein the processor is further configured to execute the instructions to:

provide a user interface for use by a user of the system; and provide, to the user by way of the user interface, information representative of the determination that the second electrode has not yet been inserted into the cochlea.

4. The system of claim 1, wherein:

the excitation spread measurement is included within a sequence of excitation spread measurements performed by the processor, the sequence of excitation spread measurements involving each of the plurality of electrodes; and the processor is further configured to execute the instructions to:

determine, based on the sequence of excitation spread measurements, whether each of the plurality of electrodes is located within the cochlea, and determine, based on the determination of whether each of the plurality of electrodes is located within the cochlea, an insertion depth of the electrode lead within the cochlea.

5. The system of claim 4, wherein the processor is further configured to execute the instructions to:

provide a user interface for use by a user of the system; and provide, to the user by way of the user interface, information representative of the determined insertion depth of the electrode lead within the cochlea.

6. The system of claim 4, wherein the processor is further configured to execute the instructions to:

detect, in real time during the insertion procedure while the electrode lead is at the determined insertion depth within the cochlea, an occurrence of an event associated with the insertion procedure; and store, in a storage facility associated with the system and in response to the detection of the occurrence of the event, a record representative of the occurrence of the event and the determined insertion depth of the electrode lead within the cochlea.

7. The system of claim 6, wherein the processor is further configured to execute the instructions to use the stored record representative of the occurrence of the event and the determined insertion depth of the electrode lead within the cochlea to facilitate a subsequent insertion procedure of another electrode lead into a cochlea of another patient.

8. The system of claim 1, wherein:

the first electrode is nearest of all the electrodes of the plurality of electrodes to a distal end of the electrode lead;

the ground contact is a ground electrode included on a proximal portion of the electrode lead that remains external to the cochlea after the insertion procedure; and the determining that the second electrode has not yet been inserted into the cochlea includes determining that the detected voltage between the second electrode and the ground contact does not exceed a predetermined threshold.

9. The system of claim 1, wherein:

the first electrode is nearest of all the electrodes of the plurality of electrodes to a distal end of the electrode lead;

the ground contact is a case ground of a cochlear implant to which the electrode lead is coupled; and the determining that the second electrode has not yet been inserted into the cochlea includes determining that the detected voltage between the second electrode and the ground contact does not exceed a predetermined threshold.

10. A system comprising:

a memory storing instructions; and a processor communicatively coupled to the memory and configured to execute the instructions to:

perform, in real time during an insertion procedure that is being performed to insert a plurality of electrodes disposed on an electrode lead into a cochlea of a patient, a sequence of excitation spread measurements comprising a particular excitation spread measurement that includes:

directing a first electrode of the plurality of electrodes to generate an electrical pulse at a particular time during the insertion procedure when the first electrode has already been inserted into the cochlea, and, in response to the generation of the electrical pulse by the first electrode, detecting a voltage between a second electrode of the plurality of electrodes that has not yet been inserted into the cochlea and a ground contact that is to remain external to the cochlea after the insertion procedure;

determine, in real time during the insertion procedure and based on the particular excitation spread measurement, that the second electrode has not yet been inserted into the cochlea at the particular time;

determine, in real time during the insertion procedure and based on the sequence of excitation spread measurements and the determination that the second electrode has not yet been inserted into the cochlea at the particular time, an insertion depth of the electrode lead within the cochlea.

11. The system of claim 10, wherein the processor is further configured to execute the instructions to:

provide, during the insertion procedure, a user interface for use by a user of the system; and provide, in real time during the insertion procedure, information representative of the determined insertion depth of the electrode lead within the cochlea to the user by way of the user interface.

12. The system of claim 10, wherein the processor is further configured to execute the instructions to:

detect, in real time during the insertion procedure and while the electrode lead is at the determined insertion depth within the cochlea, an occurrence of an event associated with the insertion procedure; and store, in a storage facility associated with the system and in response to the detection of the occurrence of the event, a record representative of the occurrence of the event and the determined insertion depth of the electrode lead within the cochlea.

13. The system of claim 12, wherein the processor is further configured to execute the instructions to use the stored record representative of the occurrence of the event and the determined insertion depth of the electrode lead within the cochlea to facilitate a subsequent insertion procedure of another electrode lead into a cochlea of another patient.

14. The system of claim 10, wherein:
the first electrode is nearest of all the electrodes of the plurality of electrodes to a distal end of the electrode lead;
the ground contact is a ground electrode included on a proximal portion of the electrode lead that remains external to the cochlea after the insertion procedure; and
the determining that the second electrode has not yet been inserted into the cochlea includes determining that the detected voltage between the second electrode and the ground contact does not exceed a predetermined threshold.

15. The system of claim 10, wherein:
the first electrode is nearest of all the electrodes of the plurality of electrodes to a distal end of the electrode lead;
the ground contact is a case ground of a cochlear implant to which the electrode lead is coupled; and
the determining that the second electrode has not yet been inserted into the cochlea include determining that the detected voltage between the second electrode and the ground contact does not exceed a predetermined threshold.

16. A method comprising:
performing, by an electrode locating system during an insertion procedure that is being performed to insert a plurality of electrodes disposed on an electrode lead into a cochlea of a patient, an excitation spread measurement by:
directing a first electrode of the plurality of electrodes to generate an electrical pulse at a particular time during the insertion procedure when the first electrode has already been inserted into the cochlea, and,
in response to the generation of the electrical pulse by the first electrode, detecting a voltage between a second electrode of the plurality of electrodes that has not yet been inserted into the cochlea and a ground contact that is to remain external to the cochlea after the insertion procedure; and determine, by the electrode locating system and based on the excitation spread measurement, that the second electrode has not yet been inserted into the cochlea at the particular time.

17. The method of claim 16, wherein:
the performing of the excitation spread measurement and the determining that the second electrode has not yet been inserted into the cochlea are performed in real time during the insertion procedure when the electrode lead is being inserted into the cochlea and is in motion with respect to the cochlea;
the excitation spread measurement is included within a sequence of excitation spread measurements performed by the electrode locating system, the sequence of excitation spread measurements involving each of the plurality of electrodes; and
the method further comprises:
determining, by the electrode locating system based on the sequence of excitation spread measurements, whether each of the plurality of electrodes is located within the cochlea, and determining, by the electrode locating system based on the determining of whether each of the plurality of electrodes is located within the cochlea, an insertion depth of the electrode lead within the cochlea.

18. The method of claim 17, further comprising:
providing, by the electrode locating system, a user interface for use by a user of the system; and
providing, by the electrode locating system to the user by way of the user interface, information representative of the determined insertion depth of the electrode lead within the cochlea.

19. The method of claim 16, further comprising:
providing, by the electrode locating system, a user interface for use by a user of the system; and
providing, by the electrode locating system to the user by way of the user interface, information representative of the determination that the second electrode has not yet been inserted into the cochlea.

20. The method of claim 16, wherein:
the first electrode is nearest of all the electrodes of the plurality of electrodes to a distal end of the electrode lead;
the ground contact is a ground electrode included on a proximal portion of the electrode lead that remains external to the cochlea after the insertion procedure; and
the determining that the second electrode has not yet been inserted into the cochlea includes determining that the detected voltage between the second electrode and the ground contact does not exceed a predetermined threshold.

* * * * *